(12) United States Patent
Butler et al.

(10) Patent No.: US 8,940,048 B2
(45) Date of Patent: Jan. 27, 2015

(54) EXPANDABLE SPINAL INTERBODY AND INTRAVERTEBRAL BODY DEVICES

(75) Inventors: Michael S. Butler, Fishers, IN (US); Daniel Predick, Chicago, IL (US)

(73) Assignee: Life Spine, Inc., Huntley, IL (US)

( * ) Notice: Subject to any disclaimer, the term of this patent is extended or adjusted under 35 U.S.C. 154(b) by 41 days.

(21) Appl. No.: 13/615,273

(22) Filed: Sep. 13, 2012

(65) Prior Publication Data

US 2013/0123924 A1    May 16, 2013

Related U.S. Application Data

(60) Continuation-in-part of application No. 12/789,257, filed on May 27, 2010, now Pat. No. 8,512,407, which is a division of application No. 11/394,719, filed on Mar. 31, 2006, now Pat. No. 7,731,751.

(60) Provisional application No. 60/666,945, filed on Mar. 31, 2005.

(51) Int. Cl.
*A61F 2/44* (2006.01)
*A61B 17/88* (2006.01)
(Continued)

(52) U.S. Cl.
CPC ............... *A61F 2/442* (2013.01); *A61F 2/446* (2013.01); *A61F 2/447* (2013.01); *A61B 17/8858* (2013.01); *A61F 2002/30163* (2013.01); *A61F 2002/30179* (2013.01); *A61F 2002/30428* (2013.01); *A61F 2002/30471* (2013.01); *A61F 2002/30507* (2013.01); *A61F 2002/30523* (2013.01); *A61F 2002/3055* (2013.01);
(Continued)

(58) Field of Classification Search
USPC .............. 606/246–249, 279; 623/17.11, 623/17.15–17.16, 23.47
See application file for complete search history.

(56) References Cited

U.S. PATENT DOCUMENTS

| 4,466,426 A | 8/1984 | Blackman |
| 4,636,217 A | 1/1987 | Ogilvie et al. |

(Continued)

FOREIGN PATENT DOCUMENTS

| WO | WO 2006/102485 | 9/2006 | |
| WO | WO 2006/105437 A2 | 10/2006 | |
| WO | WO 2009124269 A1 * | 10/2009 | ............... A61F 2/44 |

OTHER PUBLICATIONS

"Bacfuse® Spinous Process Fusion Plate Surgical Technique", © 2011, Pioneer Surgical, 12 pages.
(Continued)

*Primary Examiner* — Nicholas Woodall
*Assistant Examiner* — Larry E Waggle, Jr.
(74) *Attorney, Agent, or Firm* — Foley & Lardner LLP

(57) ABSTRACT

A device for insertion into a spinal (intervertebral or intravertebral) space is expandable from a first circumference to a second circumference through axial compression of segments of the device, particularly once the device has been properly situated within a vertebral space. The interbody/intravertebral body device is characterized by a plurality of axially stacked, individual segments that are provided on a central insertion and deployment rod. Each segment includes a central plate or body to which are pivotally attached plate or leaf structures. Pivoting of the structures provides a collapsed or unexpanded position of the first circumference and an open or expanded position of the second circumference.

20 Claims, 27 Drawing Sheets

(51) Int. Cl.
   *A61F 2/30* (2006.01)
   *A61F 2/46* (2006.01)
   *A61F 2/28* (2006.01)

(52) U.S. Cl.
   CPC .............. *A61F2002/30579* (2013.01); *A61F 2002/30594* (2013.01); *A61F 2002/30784* (2013.01); *A61F 2002/30841* (2013.01); *A61F 2002/4415* (2013.01); *A61F 2310/00017* (2013.01); *A61F 2310/00023* (2013.01); *A61F 2/4611* (2013.01); *A61F 2002/2835* (2013.01); *A61F 2002/30365* (2013.01); *A61F 2002/30367* (2013.01); *A61F 2002/30372* (2013.01); *A61F 2002/30373* (2013.01); *A61F 2002/30385* (2013.01); *A61F 2002/30387* (2013.01); *A61F 2002/30405* (2013.01); *A61F 2002/30411* (2013.01); *A61F 2002/30415* (2013.01); *A61F 2002/30438* (2013.01); *A61F 2002/30484* (2013.01); *A61F 2002/30556* (2013.01); *A61F 2002/3056* (2013.01); *A61F 2002/30596* (2013.01); *A61F 2002/30598* (2013.01); *A61F 2002/30601* (2013.01); *A61F 2002/3083* (2013.01); *A61F 2002/30831* (2013.01); *A61F 2002/4475* (2013.01); *A61F 2002/465* (2013.01)
   USPC ..................................... 623/17.15; 623/23.47

(56) References Cited

U.S. PATENT DOCUMENTS

| | | | |
|---|---|---|---|
| 5,390,683 A | 2/1995 | Pisharodi | |
| 5,645,599 A | 7/1997 | Samani | |
| 5,658,335 A | 8/1997 | Allen | |
| 5,658,337 A | 8/1997 | Kohrs et al. | |
| 5,836,948 A | 11/1998 | Zucherman et al. | |
| 5,860,977 A | 1/1999 | Zucherman et al. | |
| 5,876,404 A | 3/1999 | Zucherman et al. | |
| 6,048,342 A | 4/2000 | Zucherman et al. | |
| 6,068,630 A | 5/2000 | Zucherman et al. | |
| 6,074,390 A | 6/2000 | Zucherman et al. | |
| 6,126,689 A | 10/2000 | Brett | |
| 6,176,882 B1 | 1/2001 | Biedermann et al. | |
| 6,183,471 B1 | 2/2001 | Zucherman et al. | |
| 6,190,387 B1 | 2/2001 | Zucherman et al. | |
| 6,235,030 B1 | 5/2001 | Zucherman et al. | |
| 6,375,682 B1 | 4/2002 | Fleischmann et al. | |
| 6,409,766 B1 | 6/2002 | Brett | |
| 6,451,019 B1 | 9/2002 | Zucherman et al. | |
| 6,491,724 B1 | 12/2002 | Ferree | |
| 6,494,883 B1 | 12/2002 | Ferree | |
| 6,537,320 B1 | 3/2003 | Michelson | |
| 6,648,917 B2 | 11/2003 | Gerbec et al. | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,773,460 B2 | 8/2004 | Jackson | |
| 6,796,983 B1 | 9/2004 | Zucherman et al. | |
| 7,048,736 B2 | 5/2006 | Robinson et al. | |
| 7,087,055 B2 | 8/2006 | Lim et al. | |
| 7,101,375 B2 | 9/2006 | Zucherman et al. | |
| 7,621,950 B1 * | 11/2009 | Globerman et al. | ........ 623/17.11 |
| 7,695,513 B2 | 4/2010 | Zucherman et al. | |
| 7,731,751 B2 | 6/2010 | Butler et al. | |
| 8,048,117 B2 | 11/2011 | Zucherman et al. | |
| 8,231,656 B2 | 7/2012 | Lee et al. | |
| 8,241,330 B2 | 8/2012 | Lamborne et al. | |
| 8,343,190 B1 | 1/2013 | Mueller et al. | |
| 8,382,801 B2 | 2/2013 | Lamborne et al. | |
| 2002/0128716 A1 | 9/2002 | Cohen et al. | |
| 2003/0040746 A1 | 2/2003 | Mitchell et al. | |
| 2003/0236520 A1 | 12/2003 | Lim et al. | |
| 2004/0153156 A1 | 8/2004 | Cohen et al. | |
| 2004/0167625 A1 | 8/2004 | Beyar et al. | |
| 2005/0033437 A1 | 2/2005 | Bao et al. | |
| 2005/0070911 A1 | 3/2005 | Carrison et al. | |
| 2005/0131536 A1 | 6/2005 | Eisermann et al. | |
| 2005/0143827 A1 | 6/2005 | Globerman et al. | |
| 2005/0222681 A1 | 10/2005 | Richley et al. | |
| 2005/0228391 A1 | 10/2005 | Levy et al. | |
| 2005/0261769 A1 | 11/2005 | Moskowitz et al. | |
| 2005/0278036 A1 | 12/2005 | Leonard et al. | |
| 2006/0036258 A1 | 2/2006 | Zucherman et al. | |
| 2006/0084988 A1 * | 4/2006 | Kim | ........................ 606/61 |
| 2006/0089718 A1 | 4/2006 | Zucherman et al. | |
| 2006/0095136 A1 | 5/2006 | McLuen | |
| 2006/0189999 A1 | 8/2006 | Zwirkoski | |
| 2006/0241601 A1 | 10/2006 | Trautwein et al. | |
| 2006/0264938 A1 | 11/2006 | Zucherman et al. | |
| 2007/0142915 A1 | 6/2007 | Altarac et al. | |
| 2008/0114456 A1 | 5/2008 | Dewey et al. | |
| 2008/0140207 A1 * | 6/2008 | Olmos et al. | ............... 623/17.16 |
| 2008/0161818 A1 | 7/2008 | Kloss et al. | |
| 2008/0177391 A1 | 7/2008 | Mitchell et al. | |
| 2008/0183211 A1 | 7/2008 | Lamborne et al. | |
| 2008/0312741 A1 | 12/2008 | Lee et al. | |
| 2009/0062915 A1 | 3/2009 | Kohm et al. | |
| 2010/0241167 A1 | 9/2010 | Taber et al. | |
| 2011/0022090 A1 | 1/2011 | Gordon et al. | |
| 2011/0066186 A1 | 3/2011 | Boyer et al. | |
| 2011/0144692 A1 | 6/2011 | Saladin et al. | |
| 2011/0172709 A1 | 7/2011 | Lyons et al. | |
| 2011/0184468 A1 | 7/2011 | Metcalf et al. | |
| 2011/0224731 A1 | 9/2011 | Smisson et al. | |
| 2011/0282453 A1 | 11/2011 | Greenhalgh et al. | |
| 2011/0319997 A1 | 12/2011 | Glerum et al. | |
| 2012/0016418 A1 | 1/2012 | Chin et al. | |
| 2012/0059474 A1 | 3/2012 | Weiman | |
| 2012/0109203 A1 | 5/2012 | Dryer et al. | |
| 2012/0221051 A1 | 8/2012 | Robinson | |
| 2012/0330422 A1 | 12/2012 | Weiman | |

OTHER PUBLICATIONS

International Search Report for Application No. PCT/US06/12060, date of mailing Apr. 5, 2007, 1 page.
Written Opinion of the International Searching Authority for Application No. PCT/US06/12060, date of mailing Apr. 5, 2007, 3 pages.
International Preliminary Report on Patentability for Application No. PCT/US06/12060, date of completion Jul. 18, 2007, 3 pages.
International Search Report and Written Opinion for International Application No. PCT/US2012/057324, mail date Dec. 20, 2012, 10 pages.
Extended European Search Report for European Application No. 14159101.6, dated Jun. 18, 2014, 6 pages.

* cited by examiner

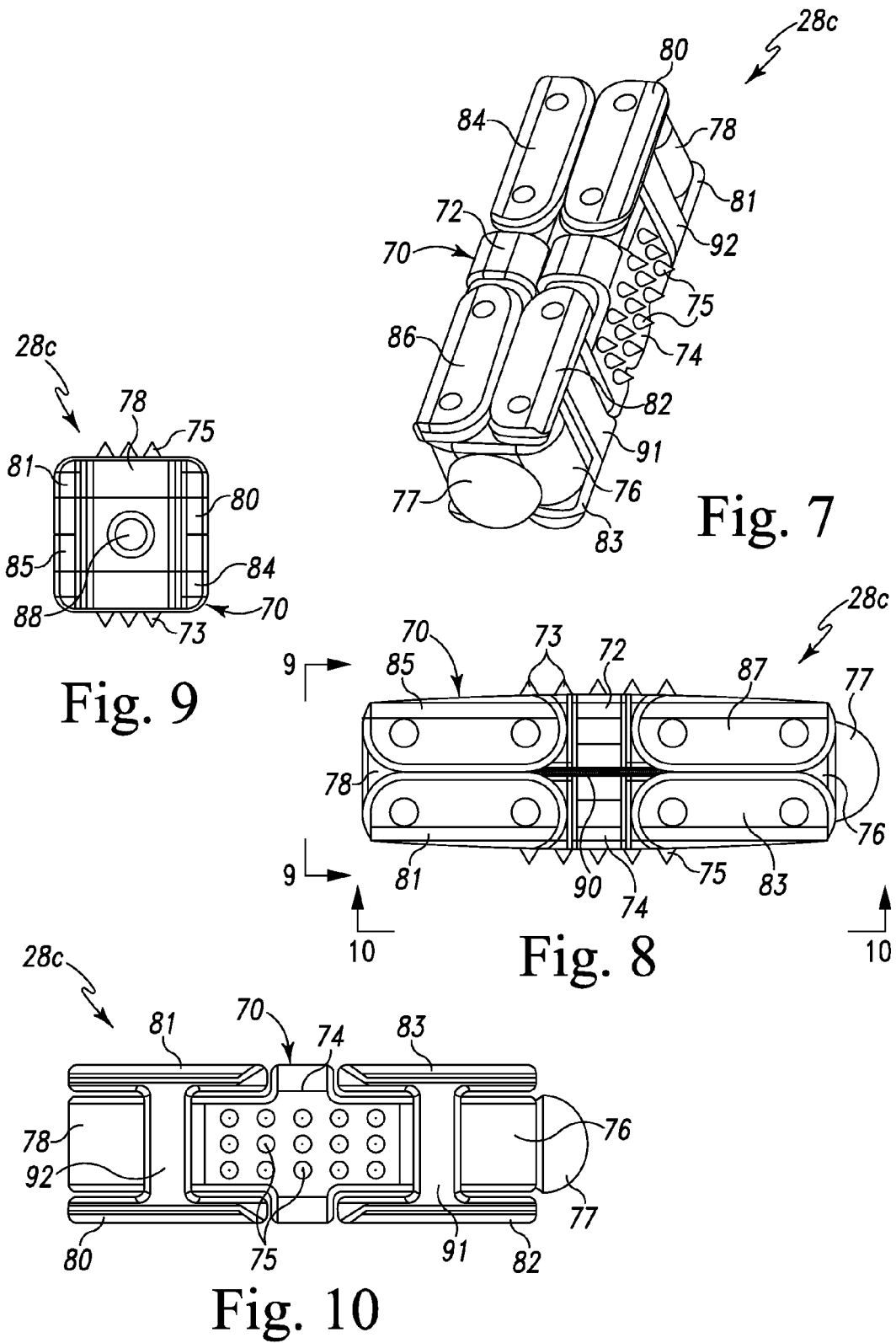

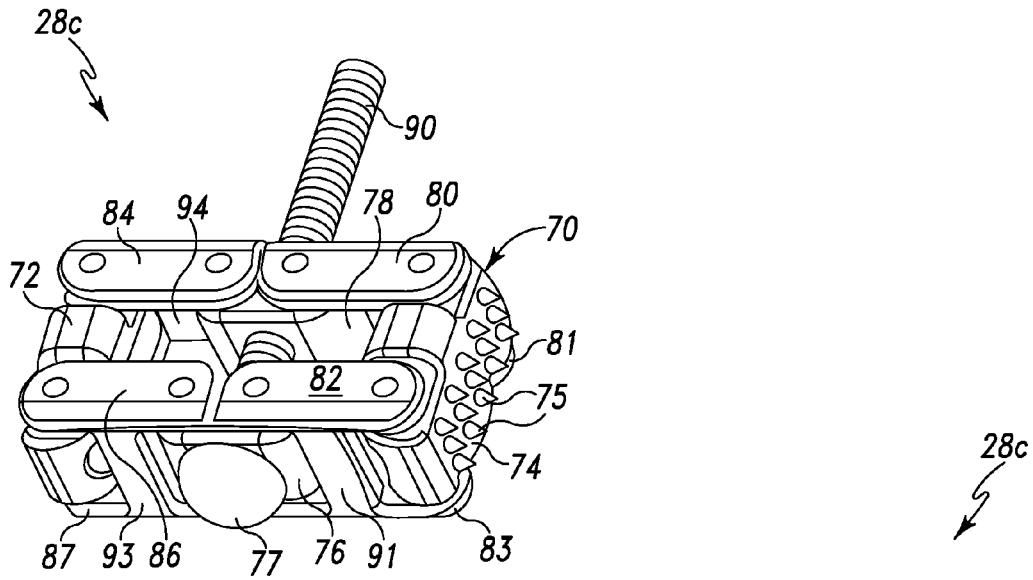
Fig. 11
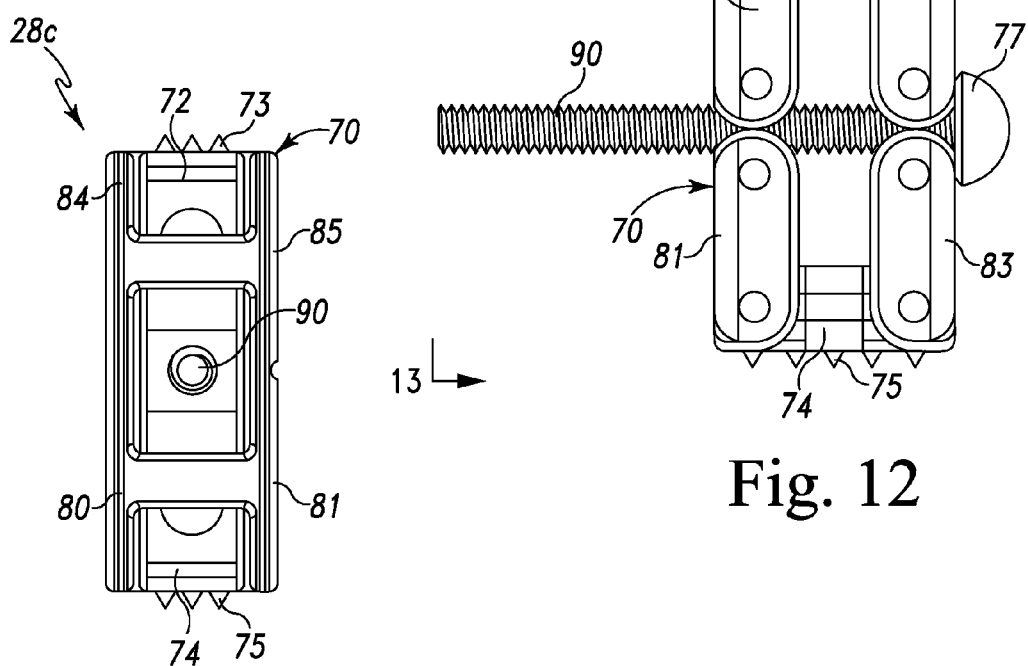
Fig. 13
Fig. 12

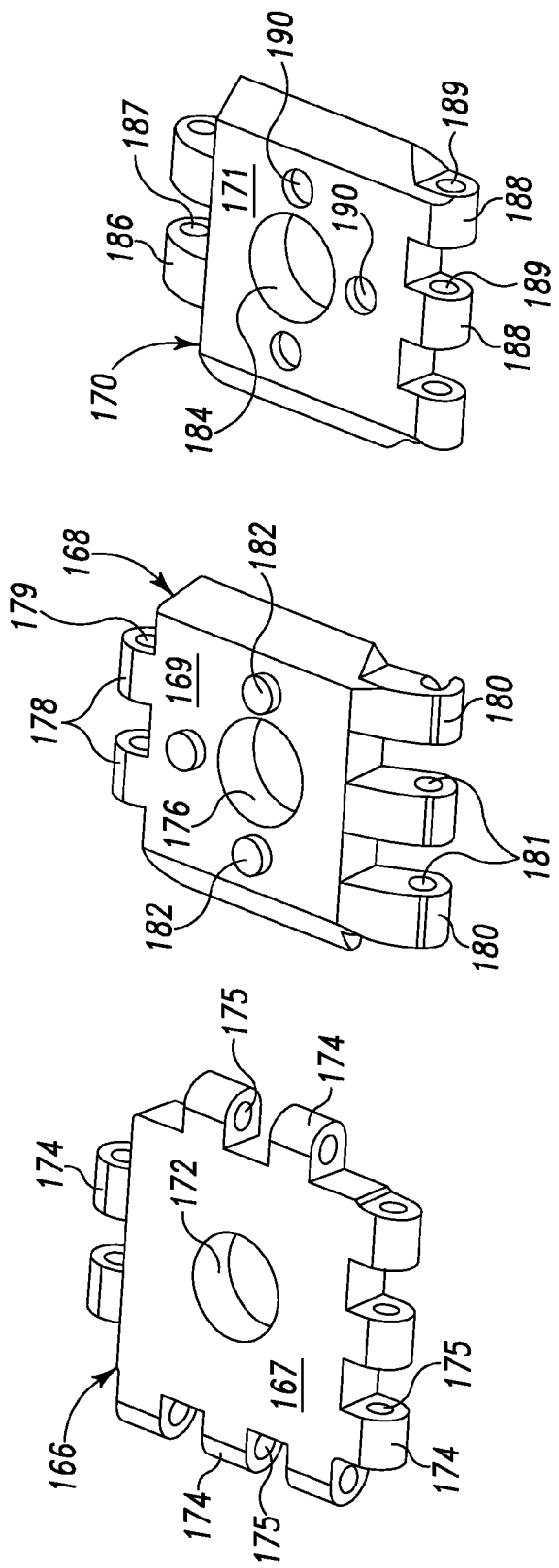

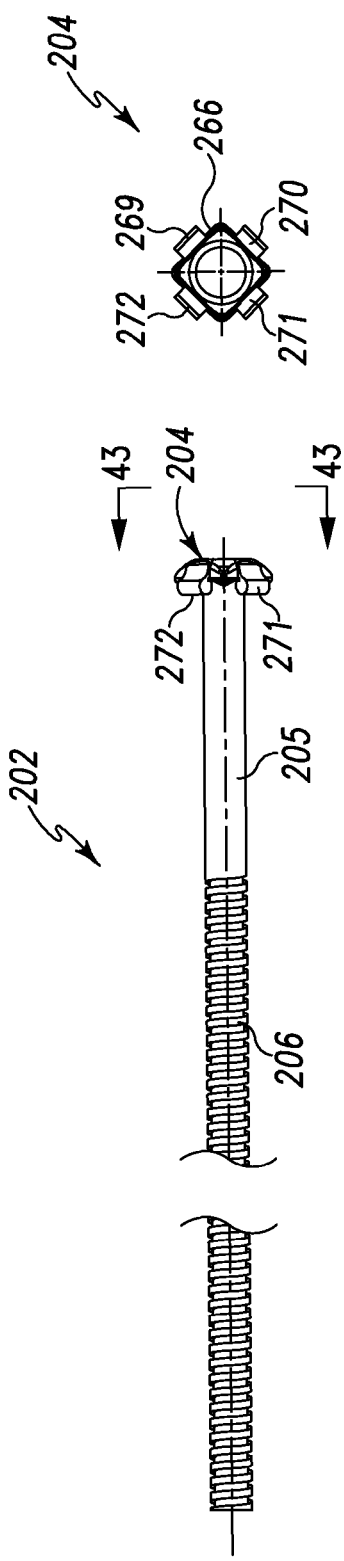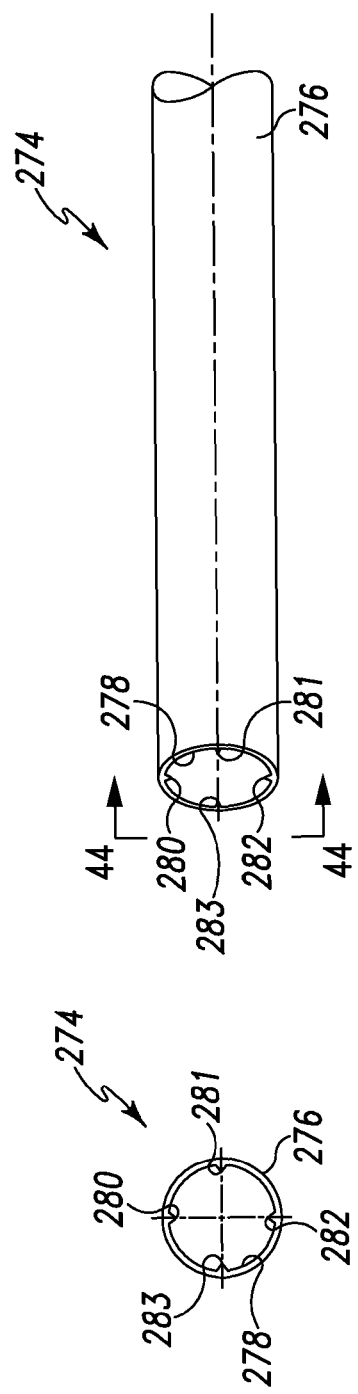
Fig. 42
Fig. 43
Fig. 44
Fig. 45

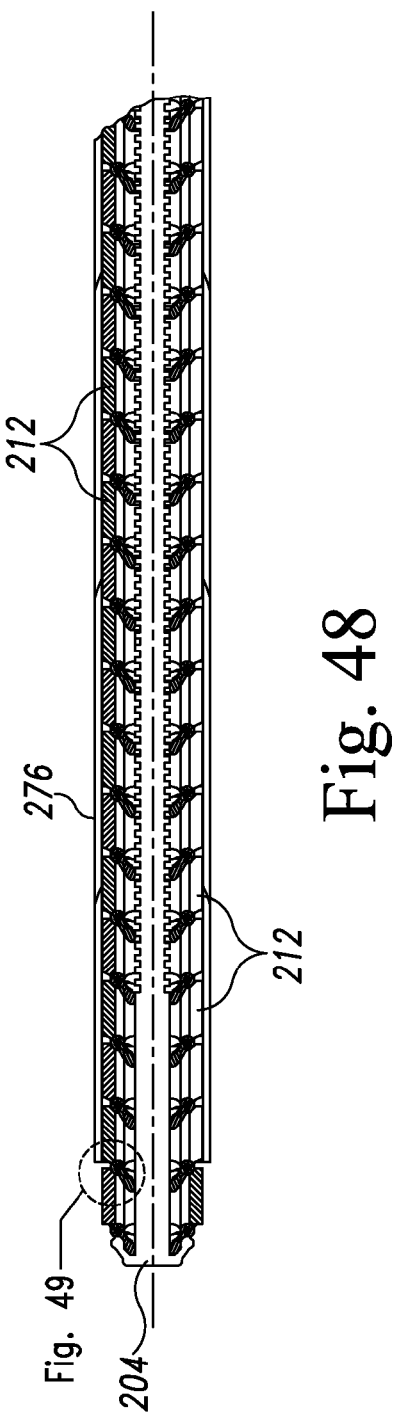
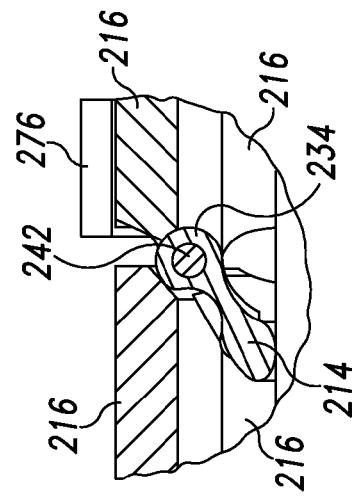
Fig. 48
Fig. 49

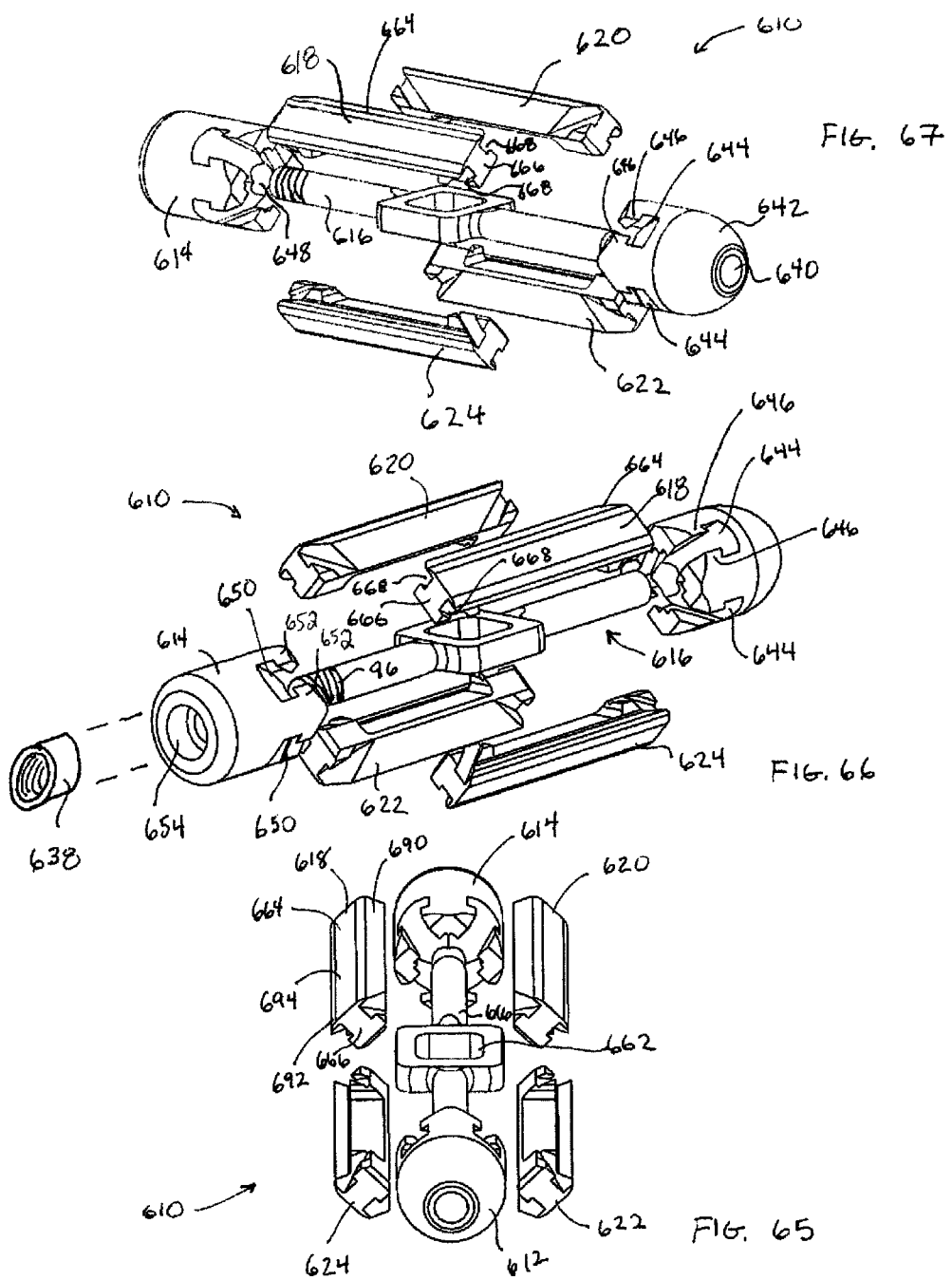

EXPANDABLE SPINAL INTERBODY AND INTRAVERTEBRAL BODY DEVICES

CROSS-REFERENCE TO RELATED PATENT APPLICATIONS

This application is a continuation-in-part of application Ser. No. 12/789,257, filed May 27, 2010, entitled "Expandable Spinal Interbody and Intravertebral Body Devices," which is a divisional application of U.S. application Ser. No. 11/394,719, filed on Mar. 31, 2006, entitled "Expandable Spinal Interbody and Intravertebral Body Devices," which claims the benefit of and/or priority to U.S. Provisional Application No. 60/666,945, filed Mar. 31, 2005, entitled "Dynamic Interbody Stabilization Devices," the entire contents of which are all hereby specifically incorporated herein by reference.

BACKGROUND

The present invention relates to spinal interbody and intravertebral body devices and, more particularly, to vertebral interbody and intravertebral devices that are expandable after spinal placement thereof.

Fusion cages, as well as other types of bodies and/or devices, are frequently utilized in spinal surgery inside a vertebra (intravertebral) and/or between vertebrae of a patient (interbody). With interbody devices, one or more such spinal bodies are placed between vertebrae to provide support and promote fusion between adjacent vertebrae where such is necessary due to disease, injury, general deterioration or congenital problem. With intravertebral devices, one or more spinal bodies are placed within a vertebra. Spinal devices, such as fusion cages and/or the like, are inserted into a spinal space either anteriorly, posteriorly, laterally or posteriolaterally.

A problem with most spinal interbody and intravertebral devices is that they are static in size. This poses various problems with their use and/or implantation. Particularly, static sized spinal devices are fairly large in order to properly bridge the gap between adjacent vertebrae. This large size does not lend itself to microsurgery, arthroscopic surgery or the like.

A few interbody devices, however, are now being made that are expandable. Expandable interbody devices allow the interbody device to be initially smaller than traditional non-expandable (static) interbody devices such that expandable interbody devices may be more easily inserted or implanted into the vertebral space. Moreover, expandable interbody devices allow the surgeon to set the amount of expansion necessary for the particular patient rather than the static interbody device dictating the spacing.

However, current expandable spinal devices lack strength, reliability and/or simplicity of design.

In view of the above, it is desirable to provide expandable spinal devices that address prior art concerns.

In view of the above, it is desirable to provide expandable spinal interbody devices that address prior art concerns.

In view of the above, it is desirable to provide expandable spinal intravertebral body devices that address prior art concerns.

SUMMARY

The present invention provides expandable spinal interbody and intravertebral body devices for insertion and maintenance between adjacent vertebrae and inside a vertebra of the spine. Particularly, the present invention provides various embodiments of expandable and/or dynamic vertebral interbody and intravertebral body devices that expand from a first radial profile into a second radial profile.

One or more of the present various expandable interbody and intravertebral devices may also provide a dynamization, mobilization or artificial disk platform. One or more of the various dynamic expandable interbody/intravertebral body devices as an artificial disk platform thus allows micro motion of the spine to occur. Additionally, one or more of the present various dynamic expandable interbody/intravertebral devices may function as a fusion device when bone, therapeutic agent or the like is included therein.

In one form, an expandable vertebral interbody/intravertebral body device for insertion into a vertebral space is provided. The interbody/intravertebral body device is expandable from a first circumference (radial profile) to a second circumference (radial profile) through axial compression of segments of the vertebral interbody/intravertebral body device, particularly once the interbody/intravertebral body device has been properly situated within a vertebral space. The interbody/intravertebral body device is characterized by a plurality of axially stacked, individual segments that are provided on a central insertion and deployment rod. Each segment includes a central plate or body to which are pivotally attached plate or leaf structures. Pivoting of the structures provides a collapsed or unexpanded position of the first circumference and an open or expanded position of the second circumference. The vertebral interbody/intravertebral body device may be formed of a bio-compatible radiolucent material. The radial profile of an interbody/intravertebral body device is easily defined by plate or leaf structures of the segments.

BRIEF DESCRIPTION OF THE DRAWINGS

The foregoing and other features of the present invention will become more apparent to one skilled in the art upon also reading the following description of embodiments with reference to the accompanying drawings wherein:

FIG. 7 is a perspective view of an exemplary embodiment of an expandable interbody/intravertebral body device in accordance with the present principles, the interbody/intravertebral body device shown in a pre-implant or unexpanded state;

FIG. 8 is a side view of the expandable interbody/intravertebral body device of FIG. 7;

FIG. 9 is a left side view of the expandable interbody/intravertebral body device of FIG. 8 taken along line 9-9 thereof;

FIG. 10 is a bottom view of the expandable interbody/intravertebral body device of FIG. 8 taken along line 10-10 thereof;

FIG. 11 is a perspective view of the expandable interbody/intravertebral body device of FIG. 7 shown in a post-implant or expanded state;

FIG. 12 is a side view of the expandable interbody/intravertebral body device of FIG. 11;

FIG. 13 is a right side view of the expandable interbody/intravertebral body device of FIG. 12 taken along line 13-13 thereof;

FIG. 20 is an enlarged perspective view of an end plate of the expandable interbody/intravertebral body segment of FIG. 18;

FIG. 21 is an enlarged perspective view of a first interconnect plate of the expandable interbody/intravertebral body segment of FIG. 18;

FIG. 22 is an enlarged perspective view of a second interconnect plate of the expandable interbody/intravertebral body segment of FIG. 18;

FIG. 42 is a side view of an implant and deploy rod for use with the expandable interbody/intravertebral body device of FIG. 23;

FIG. 43 is a right side (end) view of the rod of FIG. 42 taken along line 43-43 thereof;

FIG. 44 is an end view of an exemplary insertion and deployment cannula for the various expandable interbody/intravertebral body devices taken along line 44-44 of FIG. 45;

FIG. 45 is a side view of the exemplary insertion and deployment cannula of FIG. 44;

FIG. 48 is a sectional view of FIG. 47 taken along line 48-48 thereof;

FIG. 49 is an enlarged, sectional portion of FIG. 48;

FIG. 65 is a perspective view of the implant of FIG. 59 according to an exemplary embodiment.

FIG. 66 is another perspective view of the implant of FIG. 59 according to an exemplary embodiment.

FIG. 67 is another perspective view of the implant of FIG. 59 according to an exemplary embodiment.

Figure 1:
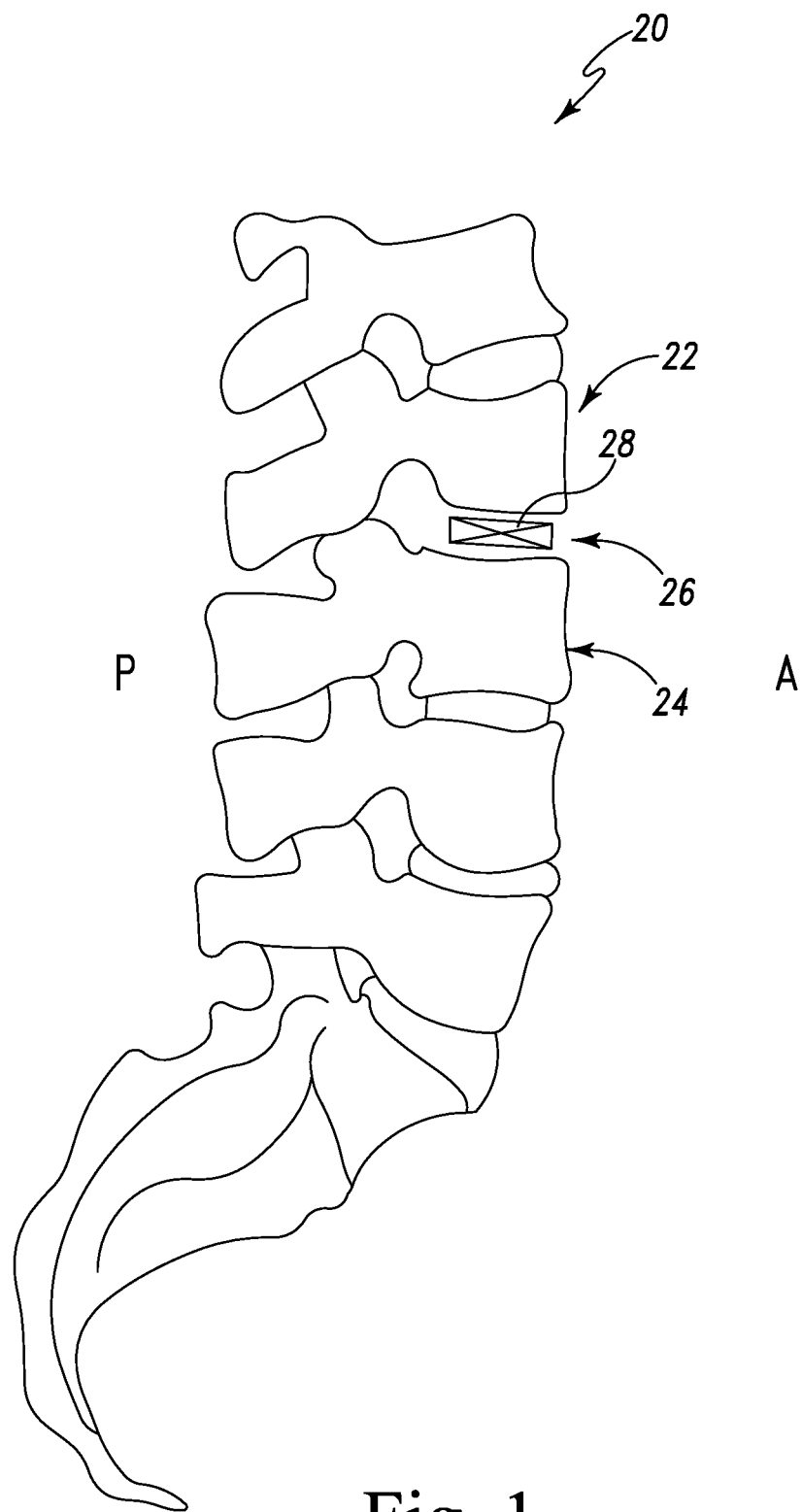
FIG. 1 is a side view of a portion of a human spine illustrating inter-vertebral placement of an expandable interbody/intravertebral body device in accordance with the principles of the present invention.

Corresponding reference characters indicate corresponding parts throughout the several views. Although the drawings represent embodiments of the invention, the drawings are not necessarily to scale and certain features may be exaggerated in order to better illustrate and explain the principles of the present invention. The exemplifications set out herein illustrate several embodiments of the invention, but the exemplifications are not to be construed as limiting the scope of the invention in any manner.

DETAILED DESCRIPTION OF EXEMPLARY EMBODIMENTS

The present invention relates to expandable and/or dynamic interbody (between adjacent vertebrae), intravertebral body devices (inside the vertebrae) and/or spinal stabilization devices that may or may not be used as interbody fusion cages or devices, interbody/intravertebral bodies/body stabilization devices and/or the like (collectively hereinafter, spinal device(s)) for providing support, stabilization and/or promoting bone growth between or inside vertebrae that have been destabilized or otherwise due to injury, illness and/or the like. Particularly, the present invention provides various versions of dynamic (expandable and/or expandable and retractable) interbody/intravertebral body devices that are usable in a spinal column of a human. As representative of each one of the various versions of the present invention, FIG. 1 illustrates a representative dynamic spinal body device 28. The spinal body 28 is depicted as implanted or inserted into a human spine of which only a lower portion 20 of the spine is shown. The spinal device 28 is illustrated implanted between adjacent upper and lower vertebrae 22, 24 of the spine portion 20 in FIG. 1 (hence interbody or intervertebral). A spinal device 28 illustrated as body 28f is shown as implanted into a vertebra (hence intravertebral body) in FIGS. 57 and 58. Vertebrae 22 and 24 have portions that face anteriorly ("A", and from the right as viewed in FIG. 1) and portions that face posteriorly ("P", and from the left as viewed in FIG. 1).

Figure 2:
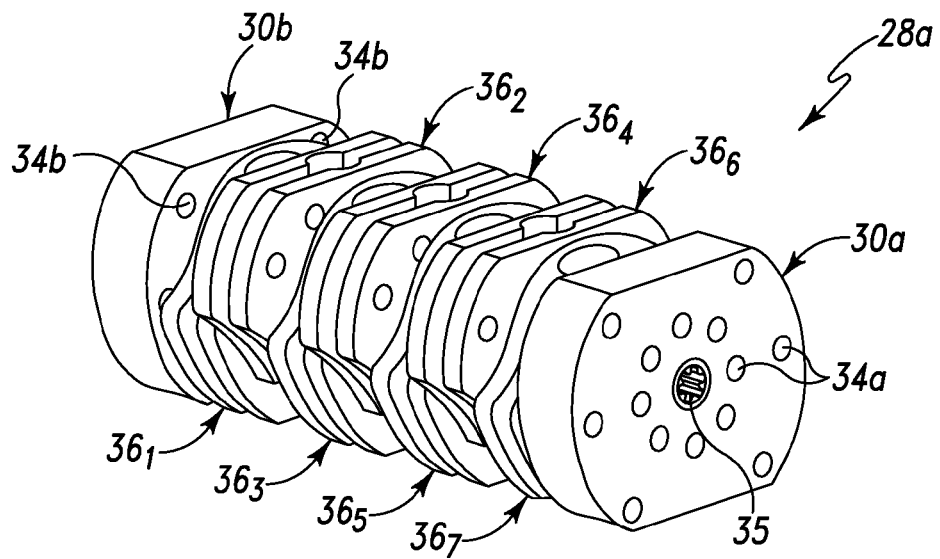
FIG. 2 is a perspective view of an exemplary embodiment of an expandable interbody/intravertebral body device in accordance with the present principles, the expandable interbody/intravertebral body device depicted in a pre-implant or unexpanded state.
Figure 3:
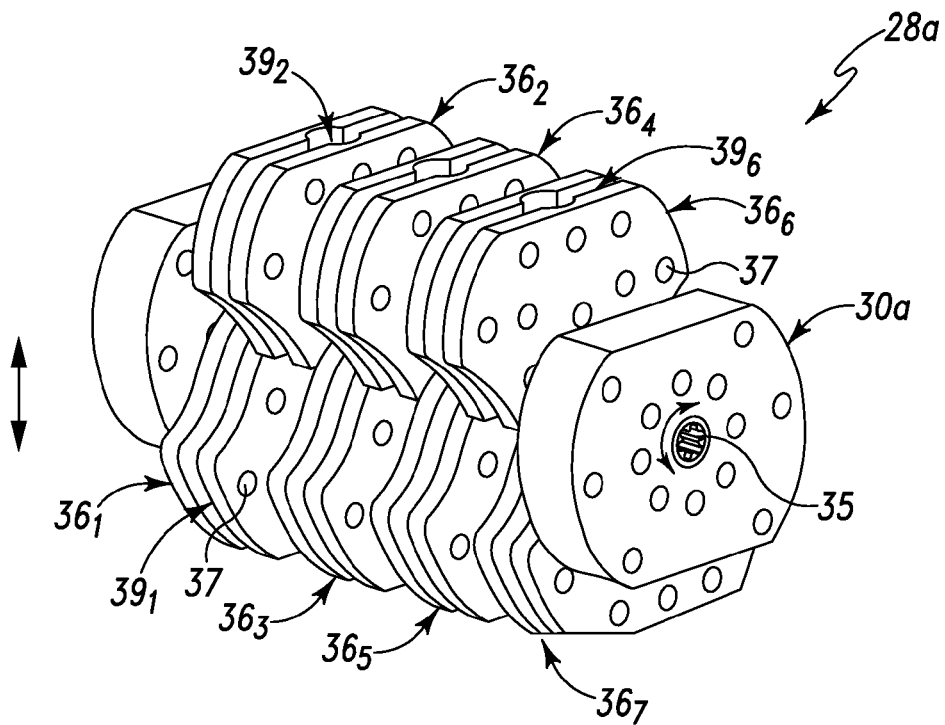
FIG. 3 is a perspective view of the expandable interbody/intravertebral body device of FIG. 2 depicted in a post-implant or expanded state.

Referring to FIGS. 2 and 3, there is depicted an embodiment of an expandable and retractable interbody/intravertebral body device generally designated 28a. FIG. 2 depicts the interbody/intravertebral body device 28a in a fully unexpanded or fully retracted position, while FIG. 3 depicts the interbody/intravertebral body device 28a in a fully expanded or fully un-retracted position. Of course, the interbody/intravertebral body device 28a may be positioned anywhere between the fully expanded to fully retracted positions.

The interbody/intravertebral body device 28a is a posterior (can be inserted in any direction) inserted interbody/intravertebral body device that provides controlled, vertical expansion within the intervertebral space 26 as well as vertical retraction within the intervertebral space 26. The interbody/intravertebral body device 28a includes identical end plates 30a, 30b each having holes or bores 34a, 34b therethrough. A central axis or shaft 35 has ends retained in each end plate 30a, 30b for rotation of the shaft 35. The ends of the shaft 35 are configured to receive a tool for rotation of the shaft and the expansion or retraction of a plurality of plates $36_1$, $36_2$, $36_3$, $36_4$, $36_5$, $36_6$, and $36_7$.

Each one of the plurality of plates 36 includes holes or bores 37. Additionally, each plate 36 is partially bifurcated creating a slot 39 in each plate. The plates 36 are connected to the shaft 35 such that one set of plates $36_1$, $36_3$, $36_5$, and $36_7$ move in one outward direction (expansion) upon shaft rotation in a first direction while another set of plates $36_2$, $36_4$, and $36_6$ move in another (opposite) outward direction (expansion) upon shaft rotation in the first direction. Shaft rotation in a second direction causes both sets of plates to retract. The adjustment of the expansion/retraction of the plates $36_1$, $36_2$, $36_3$, $36_4$, $36_5$, $36_6$, and $36_7$ is done in situ. The interbody/intravertebral body device 28a may also act as an artificial disk allowing movement.

Figure 4:
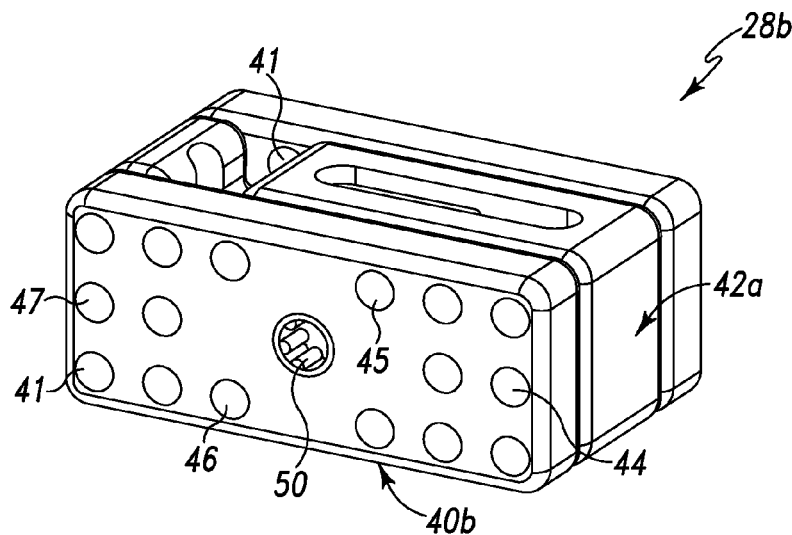
FIG. 4 is a perspective view of an exemplary embodiment of an expandable interbody/intravertebral body device in accordance with the present principles, the expandable interbody/intravertebral body device depicted in a pre-implant or unexpanded state.
Figure 5:
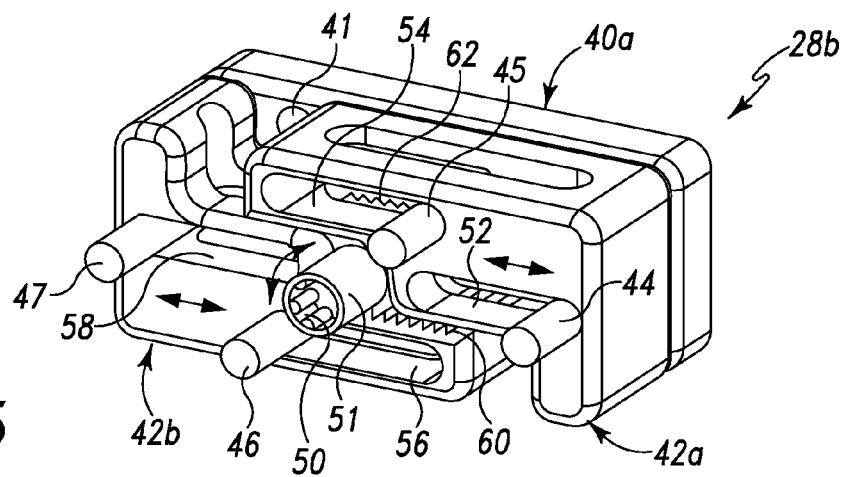
FIG. 5 is a perspective view of the expandable interbody/intravertebral body device of FIG. 4 depicted in the pre-implant or unexpanded state with a plate thereof removed for viewing of an expansion mechanism thereof.
Figure 6:
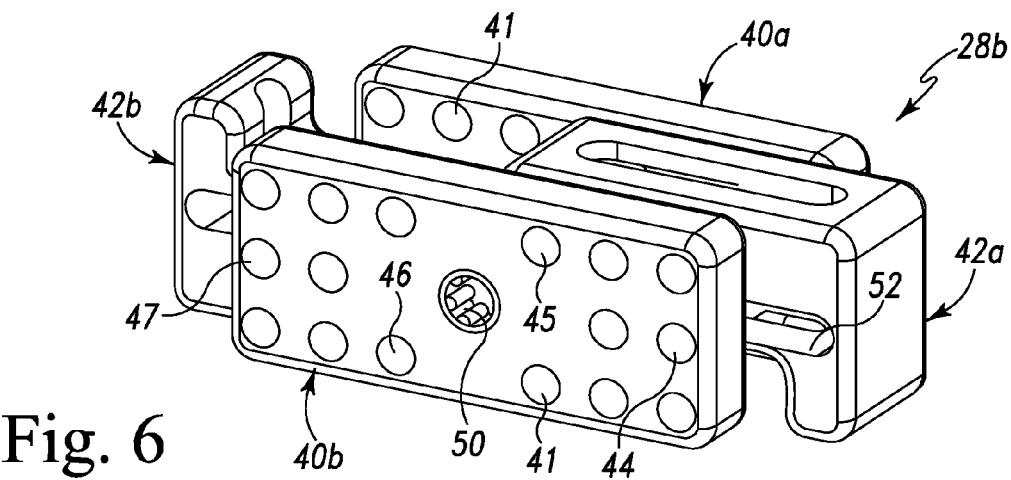
FIG. 6 is a perspective view of the expandable interbody/intravertebral body device of FIG. 4 depicted in a post-implant or expanded state.

Referring to FIGS. 4-6 there is depicted an embodiment of an expandable and retractable (dynamic) interbody/intravertebral body device generally designated 28b. FIG. 4 depicts the interbody/intravertebral body device 28b in a fully unexpanded or fully retracted position, while FIG. 6 depicts the interbody/intravertebral body device 28b in a fully expanded or fully un-retracted position. Of course, the interbody/intravertebral body device 28b may be positioned anywhere between the fully expanded to fully retracted positions. FIG. 5 depicts the manner in which the interbody/intravertebral body device 28b expands. Thus, in FIG. 5 the end plate 40b is removed for clarity in illustrating such expansion (and oppositely, contraction).

The interbody/intravertebral body device 28b is an anterior inserted interbody/intravertebral body device that provides controlled, horizontal expansion within the intervertebral space 26 as well as vertical retraction within the intervertebral space 26. The interbody/intravertebral body device 28b includes identical end plates 40a, 40b each having holes or bores 41 therein. The end plates 40a, 40b are joined together via posts 44, 45, 46 and 47. The posts 44, 45, 46 and 47 also provide a guide for the identical expansion/retraction members 42a and 42b that are retained between the end plates 40a, 40b.

Particularly, member 42a has a first slot 52 in which post 44 is situated, and a second slot 54 in which post 45 is situated. The slots and posts define the length of travel for the member 42a when the keyed shaft 50 is rotated. As well, the member 42b has a first slot 56 in which post 46 is situated, and a second slot 58 in which post 47 is situated. The slots and posts define the length of travel for the member 42b when the keyed shaft 50 is rotated.

The shaft 50 includes knurls or teeth 51 on an outside thereof that co-act with teeth 60 of member 42a and teeth 62 of the member 42b. Rotation of the shaft 50 in a first radial direction moves the members 42a and 42b in opposite and outward direction. Rotation of the shaft 50 in a second direction (opposite the first direction) moves the members 42a and 42b inwardly.

Referring to FIGS. 7-13 there is depicted another embodiment of an interbody/intravertebral body device generally designated 28c. The interbody/intravertebral body device 28c is shown in a pre-implant or unexpanded/collapsed state in FIGS. 7-10 and in a post-implant or expanded state in FIGS. 11-13. The interbody/intravertebral body device 28c is characterized by a body 70 having a first end plate 72 and a second end plate 74. The first end plate 72 includes a plurality of grips or spikes 73. The second end plate 74 also includes a plurality of grips or spikes 75. The spikes 73, 75 are shown as cone-shaped but may take on other forms. The spikes 73, 75 are designed to grip or extend into adjacent vertebrae.

The interbody/intravertebral body device 28c also includes a first side component 76 and a second side component 78. The first end plate 72 is pivotally connected at one side thereof to the first side component 76 by a first hinge component 93 via hinge plates 86 and 87 of the first hinge component 93, and pivotally connected at another side thereof to the second side component 78 by a second hinge component 94 via hinge plates 84 and 85 of the second hinge component 94. In like manner, the second end plate 74 is pivotally connected at one side thereof to the first side component 76 by a third hinge component 91 via hinge plates 82 and 83 of the third hinge component 91, and pivotally connected at another side thereof to the second side component 78 by a fourth hinge component 92 via hinge plates 80 and 81 of the fourth hinge component 92.

The interbody/intravertebral body device 28c further includes an expansion/contraction member (threaded shaft or screw) 90 that extends through a bore 88 of the second side component 78 and into the head 77 associated with the first side component 76. Expansion of the interbody/intravertebral body device 28c from the collapsed position as depicted in FIGS. 7-10 to the fully expanded position depicted in FIGS. 11-13 is accomplished by pushing the first and second side components 76 and 78 towards each other. As the threaded shaft 90 is rotated, the first and second side components 76, 78 are drawn towards one another. This pivots the first and second end plates 72 and 74 away from each other via the first, second, third and fourth hinge components 93, 94, 91, and 92 respectively.

The interbody/intravertebral body device 28c may be dimensioned as necessary. However, currently it has been found that an optimum implant footprint is approximately 6.35 mm by 9.00 mm. Moreover, the interbody/intravertebral body device 28c is preferably, but not necessarily, dimensioned to have an optimal distraction of 16.00 mm and a maximum distraction of 22.00 mm. As such, the interbody/intravertebral body device 28c is deliverable (implantable) via a minimally invasive tube delivery (e.g. 8 mm tube delivery). Furthermore, the expansion member (e.g. screw) is designed to be a torque limiting break-away screw.

Figure 14:
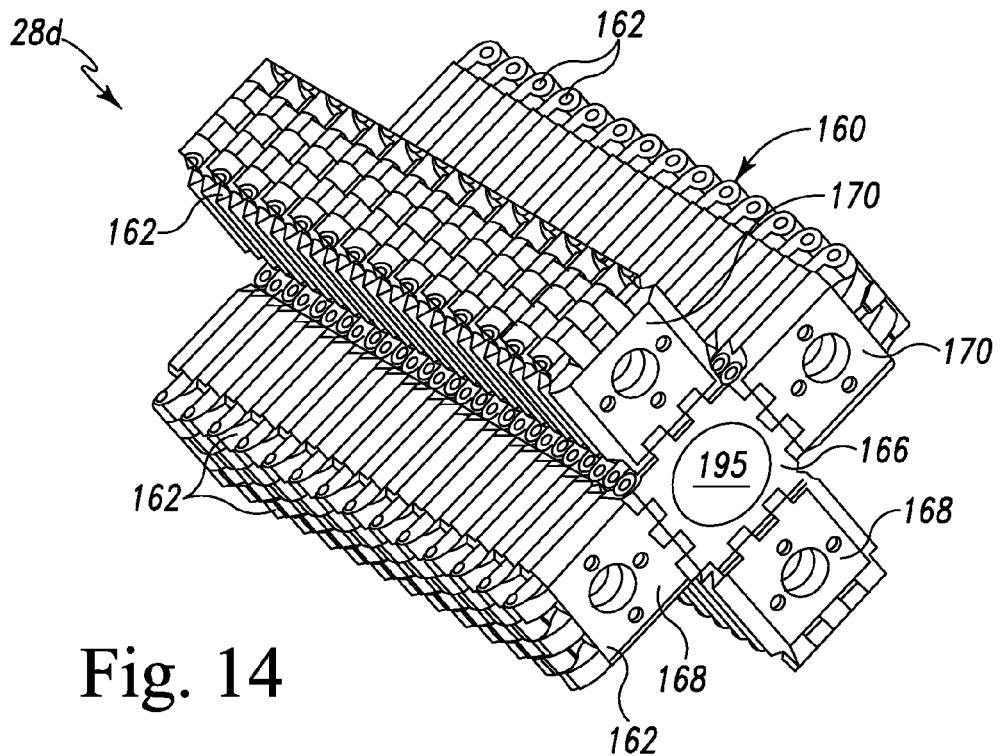
FIG. 14 is front a perspective view of an exemplary embodiment of an expandable interbody/intravertebral body device in accordance with the present principles, the interbody/intravertebral body device shown in a post-implant or expanded state.
Figure 15:
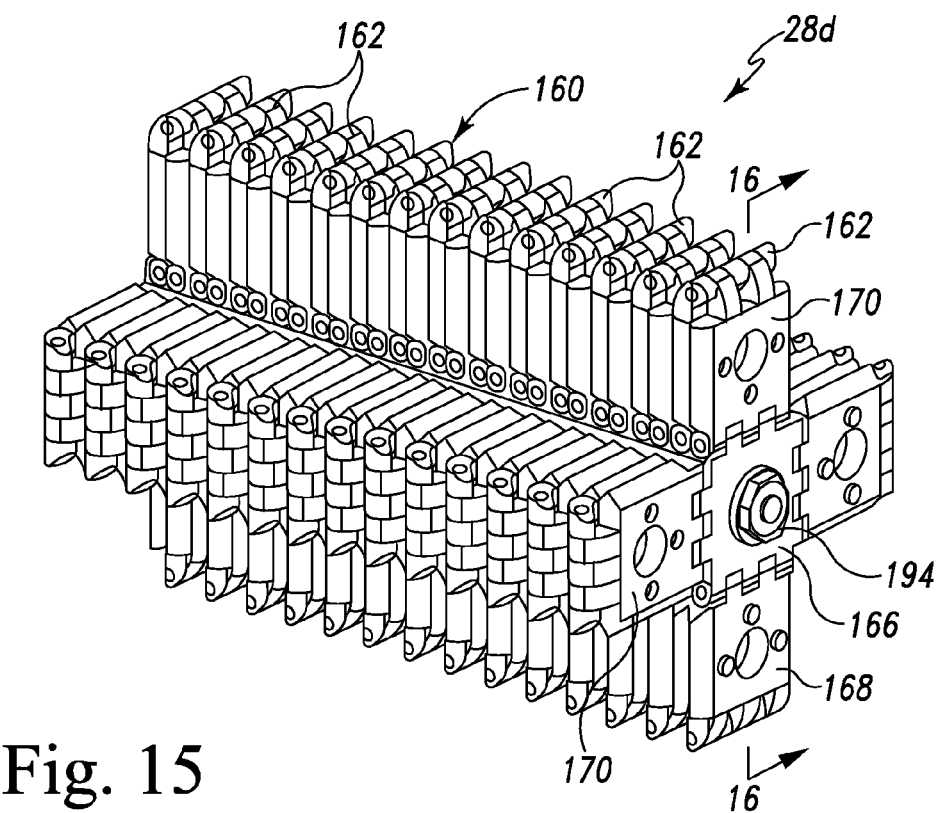
FIG. 15 is a rear perspective view of the expandable interbody/intravertebral body device of FIG. 14.
Figure 17:
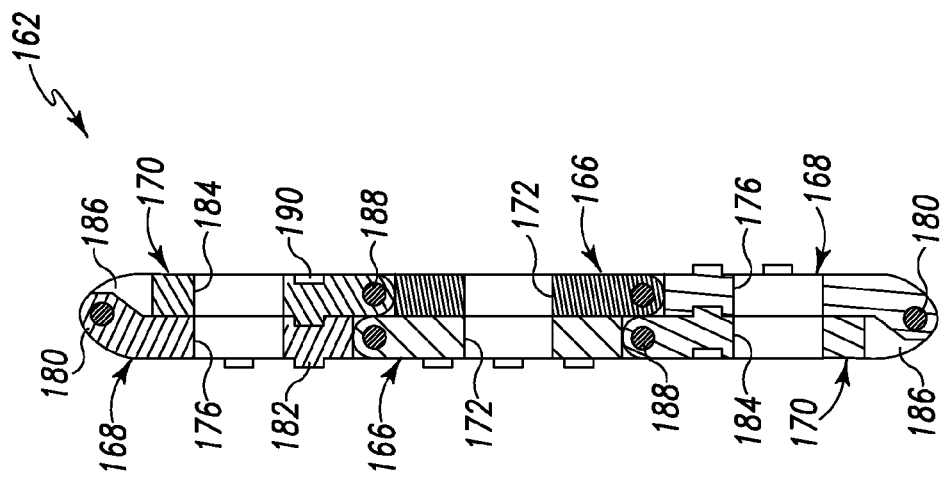
FIG. 17 is an enlarged sectional view of a single segment, section or petal of the expandable interbody/intravertebral body device of FIG. 16, the single segment shown in an expanded position.
Figure 16:
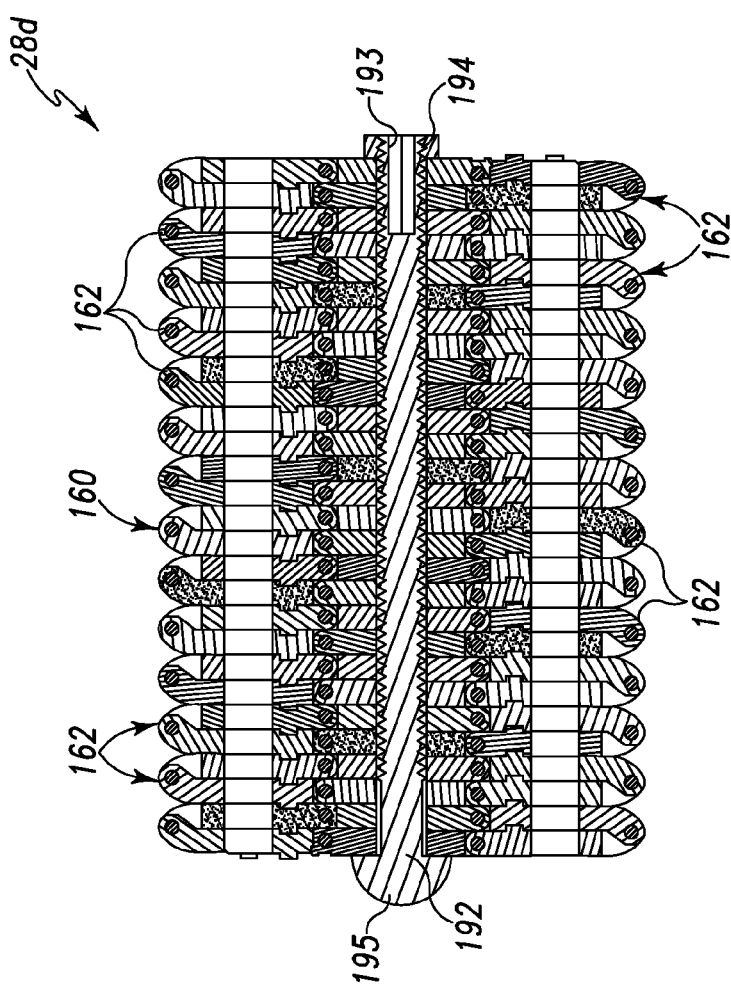
FIG. 16 is a sectional view of the expandable interbody/intravertebral body device of FIG. 15 taken along line 16-16 thereof.
Figure 18:
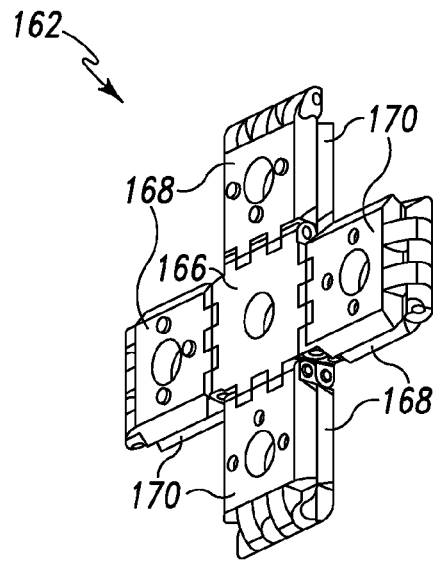
FIG. 18 is a perspective view of the single segment of FIG. 17.
Figure 19:
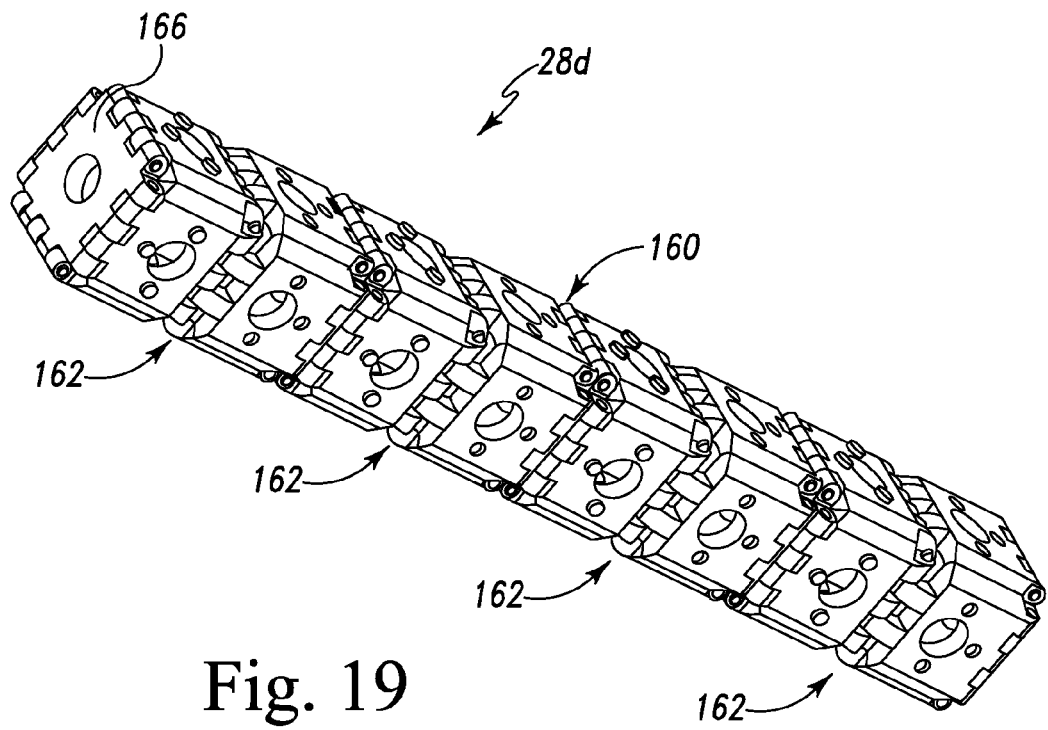
FIG. 19 is a perspective view of a plurality of expandable interbody/intravertebral body segments axially situated one to another forming an implant, the segments shown in a pre-implant or unexpanded state.

Referring to FIGS. 14-22 there is depicted another dynamic interbody/intravertebral body device generally designated 28d. The interbody/intravertebral body device 28d is characterized by a body structure 160 formed by a plurality of dynamic (expands and contracts) sections or portions 162. In FIGS. 14-16, the interbody/intravertebral body device 28d is shown in an expanded or (post) implanted state. In FIG. 19, the interbody/intravertebral body device 28d is shown in a collapsed, folded or pre implant state. In like manner, FIG. 18 depicts one section 162 in an expanded state Each section 162 is formed from three basic plates or components; i.e. an end plate 166 (see FIG. 20) used as a front plate and a back plate, a first inter-connect plate 168 (see FIG. 71) used as type I side plates, and a second inter-connect plate 170 (see FIG. 72) used as type II side plates. The various plates 166, 168 and 170 are pivotally or hingedly coupled to one another to form a section 162 such that the unexpanded box-like structure of each section collapses or folds into an expanded state.

Referring specifically to FIG. 20, end plate 166 is characterized by a rectangular and preferably, but not necessarily, generally square body 167 having a central bore 172. The body 167 includes a plurality of like hinge flanges 174 each having a hinge bore 175 therethrough for receiving a hinge pin. The body 167 includes a first side having three hinge flanges 174, a second side adjacent the first side and having three hinge flanges 174, a third side adjacent the second side (and opposite the first side) and having two hinge flanges 174, and a fourth side adjacent the third and first sides (and opposite the second side) and having two hinge flanges 174.

Referring specifically to FIG. 21, first inter-connect plate 168 is characterized by a rectangular and preferably, but not necessarily, generally square body 169 having a central bore 176. The body 169 includes two hinge flanges 178 of a first configuration each having a hinge bore 179 therethrough for receiving a hinge pin. The two hinge flanges 178 are disposed on one side of the body 169. The body 169 also includes three hinge flanges 180 of a second configuration each having a hinge bore 181 therethrough for receiving a hinge pin disposed on a side of the body 169 opposite the two hinge flange side. Additionally, the body 169 includes a plurality (here shown as three) semi-perf locaters 182 having a raised portion on one side and an indentation on the other side.

Referring specifically to FIG. 22 second inter-connect plate 170 is characterized by a rectangular and preferably, but not necessarily, generally square body 171 having a central bore 184. The body 171 includes two hinge flanges 186 of a first configuration each having a hinge bore 187 therethrough for receiving a hinge pin. The two hinge flanges 186 are disposed on one side of the body 171. The body 171 also includes three hinge flanges 188 of a second configuration each having a hinge bore 189 therethrough for receiving a hinge pin disposed on a side of the body 171 opposite the two hinge flange side. Additionally, the body 171 includes a plurality (here shown as three) semi-perf locaters 190 having a raised portion on one side and an indentation (seen in FIG. 22)

on the other side. The semi-perf locators help lock the parts together when the section is expanded. Holes and taper pins may also be used.

The expandable interbody/intravertebral body device 28d may be termed a quad directional interbody/intravertebral body device (e.g. fusion cage) or intervertebral device (e.g. interbody/intravertebral body) that is constructed with interlocking, hinged segments. The expandable interbody/intravertebral body device 28d has an implant footprint (distraction size) of 18.00 mm×18.00 mm (for a size 7 inner segment size). The expandable interbody/intravertebral body device 28d provides push action delivery. A minimally invasive (8 mm) tube delivery may be used. Segments or sections (262) may be added as needed. Preferably, the interbody/intravertebral body device 28d is fashioned from all titanium, but may be fashioned from other biocompatible material. When distracted, there is a 2 mm segment width. The interbody/intravertebral body device 28d may be provided in various sizes ranging from a size 1 through a size 7 with the size 1 having an inner segment size of 4.44 mm and distraction size of 12.00 mm, the size 2 having an inner segment size of 4.81 mm and distraction size of 13.00 mm, the size 3 having an inner segment size of 5.18 mm and distraction size of 14.00 mm, the size 4 having an inner segment size of 5.55 mm and distraction size of 15.00 mm, the size 5 having an inner segment size of 5.92 mm and distraction size of 16.00 mm, the size 6 having an inner segment size of 6.29 mm and distraction size of 17.00 mm, and the size 7 having an inner segment size of 6.66 mm and distraction size of 18.00 mm.

After insertion of the pre-implant structure, a threaded rod 192 having retained the pre-implant structure together during implantation via a head 195, is drawn out by a tool inserted into bore 193 to force the sections 162 to collapse and thus expand. A nut 194 is threadedly received on an exposed end of the rod 192 to retain the body 160 in the expanded state.

Referring to FIGS. 23-51 there is depicted another embodiment of an expandable vertebral interbody/intravertebral body device generally designated 28e. The expandable interbody/intravertebral body device 28e is radially expandable upon axial compression. Radial expansion provides vertical (co-spinal) height within a vertebral body area (see e.g. FIG. 1 area 26). Thus, the interbody/intravertebral body device 28e is characterized by the ability to be inserted or implanted into an open vertebral space in a folded or unexpanded, radially compact state or position and then be unfolded or expanded. The interbody/intravertebral body device 28e is formed of titanium, stainless steel or other biocompatible material, including composites, plastics and/or the like. Radiolucent materials may also be used and, the interbody/intravertebral body device 28e (as well as the other interbody/intravertebral body devices herein) may be formed entirely of a radiolucent material.

Figure 23:
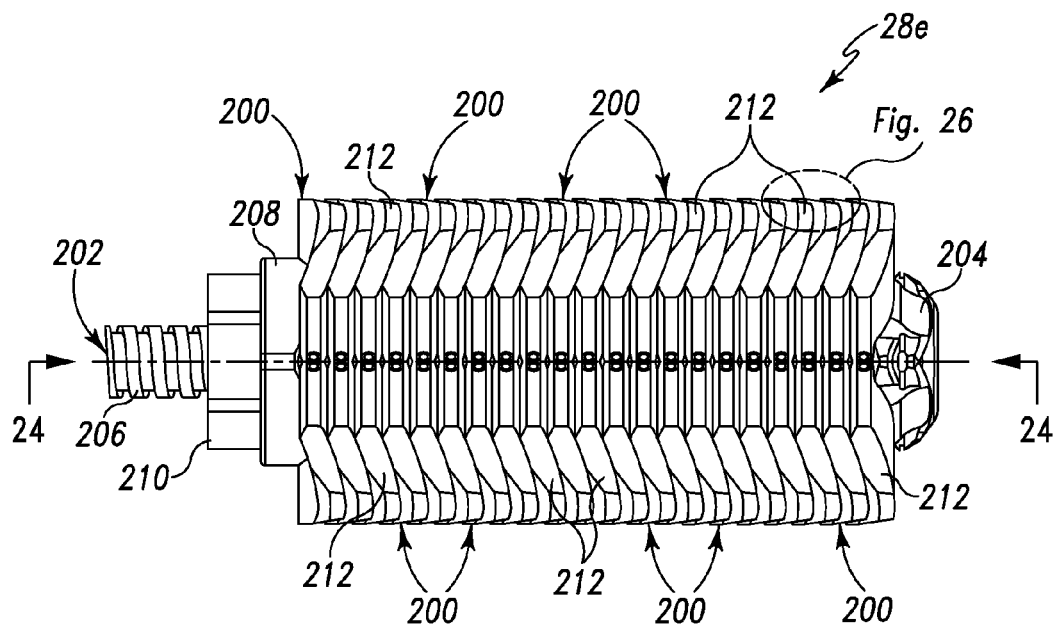
FIG. 23 is a side view of an exemplary embodiment of an expandable interbody/intravertebral body device in accordance with the present principles, the expandable interbody/intravertebral body device shown in a post-implant or expanded state.
Figure 24:
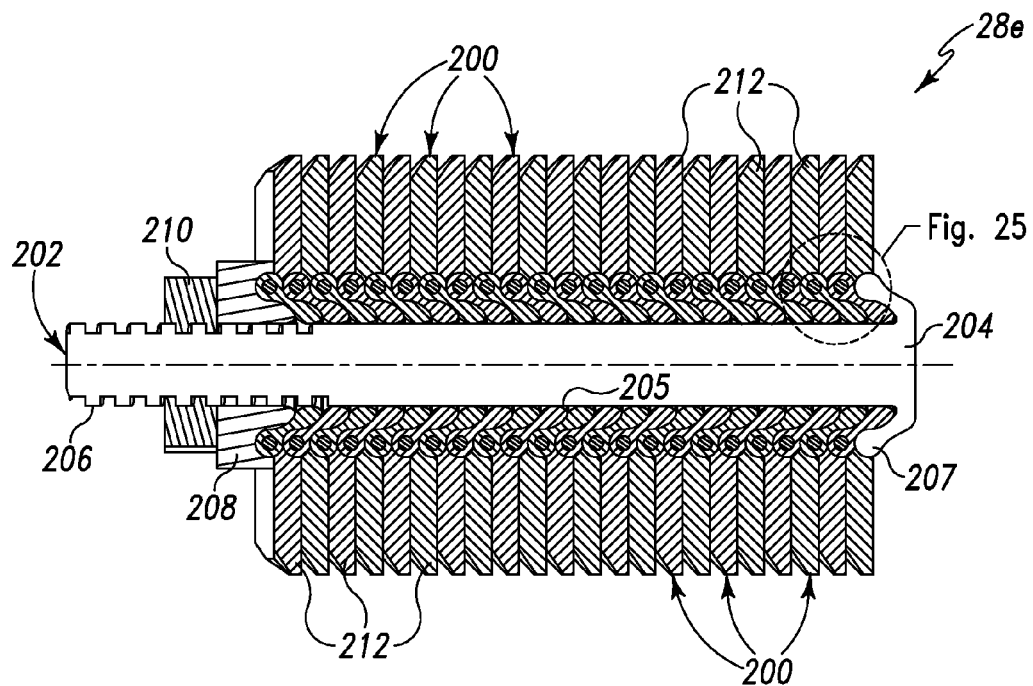
FIG. 24 is a cross-sectional view of the expandable interbody/intravertebral body device of FIG. 23 taken along line 24-24 thereof.
Figure 27:
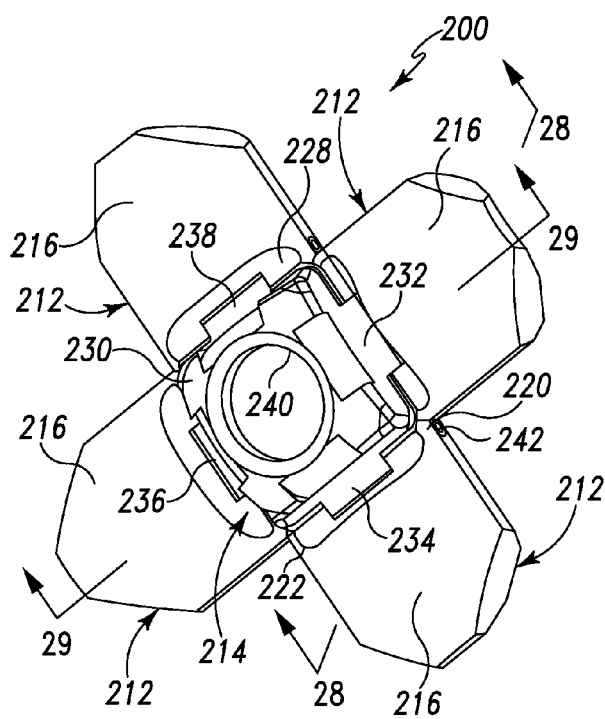
FIG. 27 is an enlarged perspective view of a segment or section of the expandable interbody/intravertebral body device of FIG. 23 in an expanded state.
Figure 30:
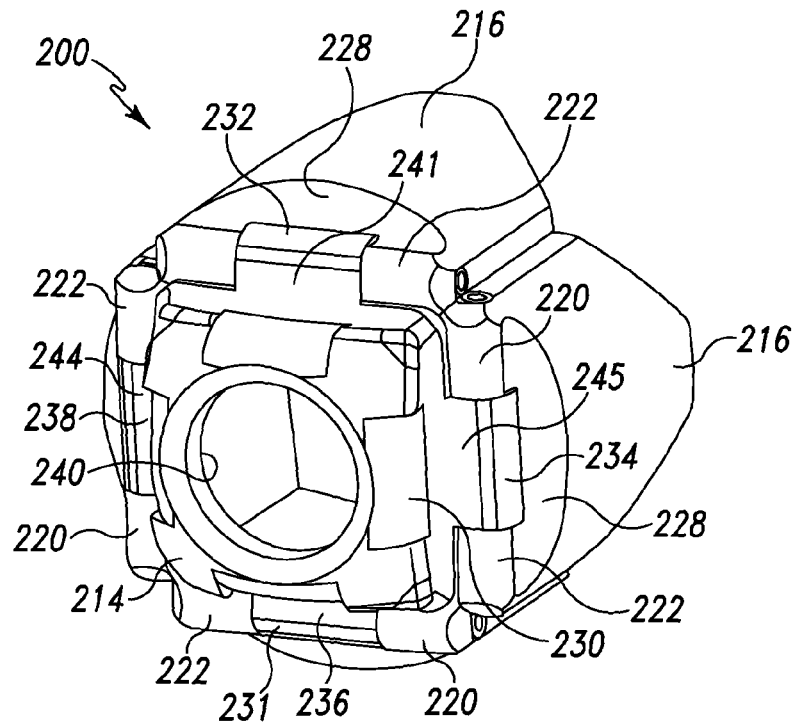
FIG. 30 is an enlarged perspective view of the interbody/intravertebral body segment of FIG. 27 shown in a folded or retracted state.
Figure 46:
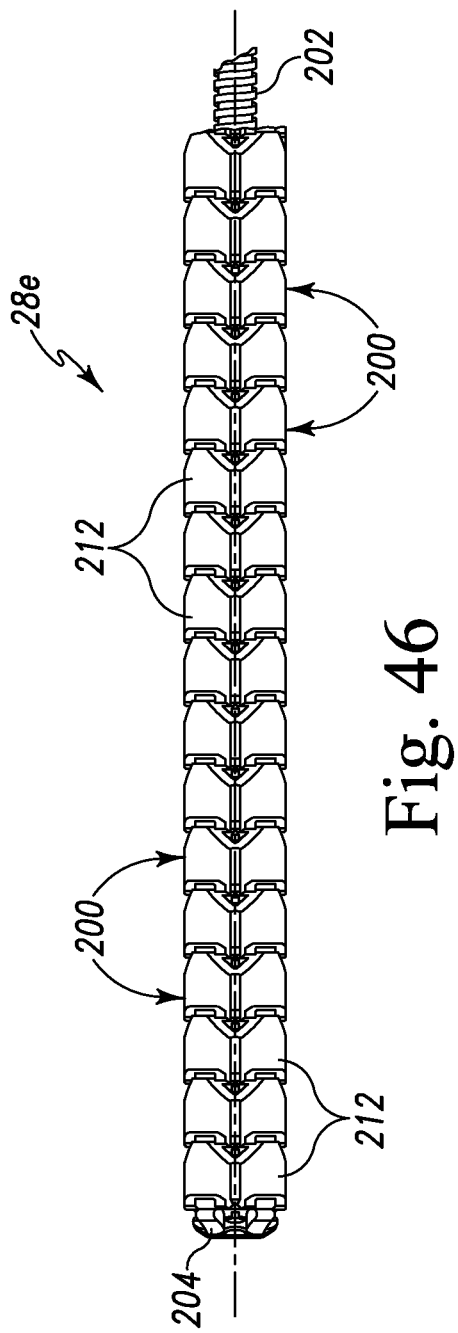
FIG. 46 is a side view of the expandable interbody/intravertebral body device of FIG. 23 in a folded position.

The interbody/intravertebral body device 28e is shown in an expanded position in FIGS. 23 and 24. The interbody/intravertebral body device 28e is characterized by a plurality of segments or sections 200 that each individually expand from a collapsed or unexpanded position into an extended or expanded position to form a vertebral interbody/intravertebral body device. FIG. 46 depicts the interbody/intravertebral body device 28e in a collapsed, folded or pre-deployment position such as after being assembled for introduction or insertion into a vertebral space. FIG. 27 depicts a segment 200 in an expanded or open position such as is seen in FIGS. 23 and 24. FIG. 30 depicts a segment 200 in a collapsed or folded position. The expandable vertebral interbody/intravertebral body device 28e is thus composed of a plurality of segments 200, the number and width thereof defining the overall axial length of the interbody/intravertebral body device 28e when expanded, with the number and axial length of leaves 212 (see, e.g. FIGS. 37-41) of the segments 200 defining the overall radial height of the interbody/intravertebral body device 28e when expanded.

The plurality of segments 200 is carried on an insertion and deployment rod 202. A deploy head or cap 204 is provided at the end of the rod 202 and is preferably integral therewith. The deploy head 204 is configured to engage, cooperate and interact with a central or middle deploy plate 214 of the segment 200. Particularly, a flange structure 207 of the rod 202 engages respective grooves (see FIG. 35 wherein three grooves 241, 244 and 245 of the four grooves of the deploy plate 214 are shown) of the deploy plate 214 (see also FIG. 25). The flange structure 207 represented in FIG. 24 is illustrated in FIGS. 42 and 43. The flange structure of the head 204 consists of four flanges 269, 270, 271 and 272 carried on a rectangular body 266. The four flanges are respectively received in the four grooves of the deploy plate 214. As described further below, axial compression of the deploy plate of the segment and the head of the rod causes the leaves 212 to pivot from an axial position to a position perpendicular to the axial position.

As best seen in FIG. 42, the rod 202 has a threaded shaft portion 206 and a non-threaded shaft portion 205. The non-threaded shaft portion 205 allows the segments 200 to axially slide during expansion of the segments 200. The threaded portion 206 threaded receives the nut 210 allows it to provide the axial force for axial compression of the segments 200 and the expansion thereof.

An end cap 208 is provided on the rod 202 distal from the head 204 of the rod 202 and between the nut 210 and the last (from left to right) deploy plate 214 of the last segment 200. The end cap 208 abuts against the central deploy plate 214 of the last segment 200. The nut 210 abuts the end cap 208. Particularly, the end cap 208 has four grooves 249, 251, 253 and 255 (see FIG. 33) that correspond to the four tubular flanges or hinge structures (which will be referred to as tubular hinge structures 232, 234, 236 and 238) of the central deploy plate 214. The tubular hinge structures of the deploy plate 214 are nested or received into the grooves of the end plate 208. Moreover, a threaded nut 210 is provided on the rod 202 to provide axial compression of the segments 200 when threadedly advanced toward the head 204 of the rod 202 to achieve radial expansion of the interbody/intravertebral body device 28e. This is done after proper placement of the interbody/intravertebral body device 28e into a vertebral space 26.

Figure 33:
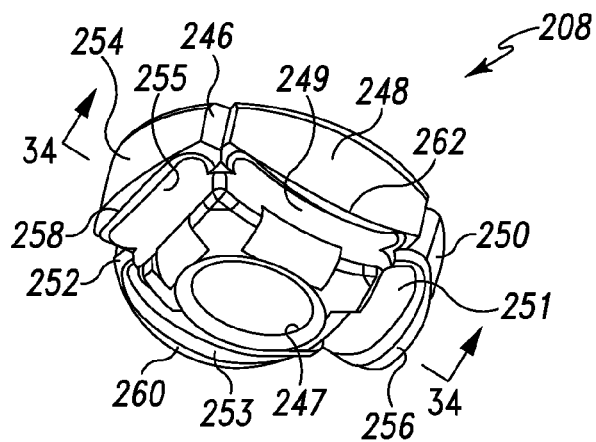
FIG. 33 is a perspective view of an end plate of the expandable interbody/intravertebral body device of FIG. 23.
Figure 34:
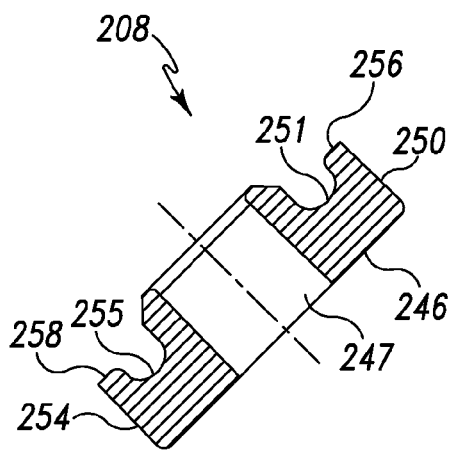
FIG. 34 is a sectional view of the end plate of FIG. 33 taken along line 34-34 thereof.

As seen in FIGS. 33 and 34, the end cap 208 is particularly characterized by a body 246 having a central or middle bore 247 that is sized to be received onto the rod 202. The body 246 defines four flanges 248, 250, 252 and 254 on sides thereof. The four flanges 248, 250, 252 and 254 each defining a respective groove 249, 251, 253 and 255 and a respective contact surface 262, 256, 260 and 258. The grooves 249, 251, 253 and 255 providing a contact surface for the tubular hinge structures 232, 234, 236 and 238 of the deploy plate 214.

Figure 26:
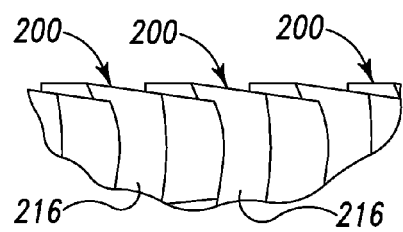
FIG. 26 is an enlarged portion of the side view of the expandable interbody/intravertebral body device of FIG. 23.
Figure 25:
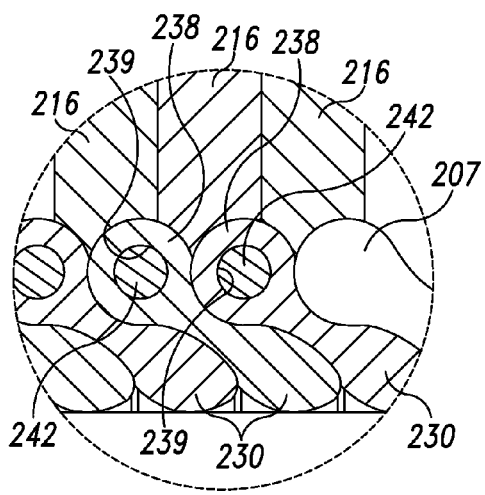
FIG. 25 is an enlarged portion of the sectional view of the expandable interbody/intravertebral body device of FIG. 24.
Figure 28:
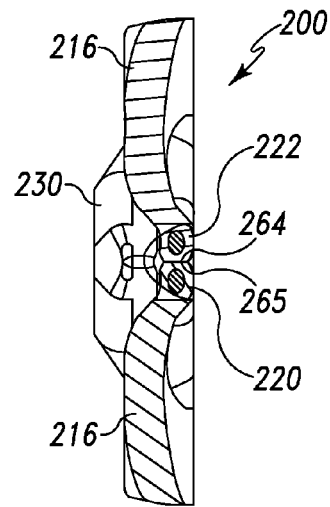
FIG. 28 is a sectional view of the interbody/intravertebral body segment of FIG. 27 taken along line 28-28 thereof.
Figure 29:
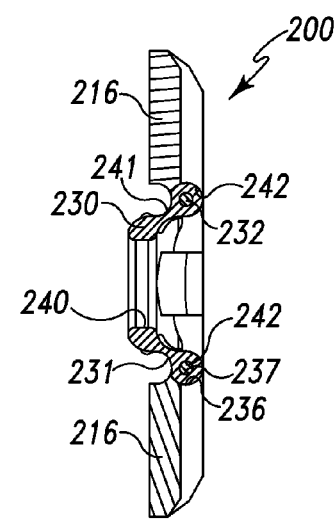
FIG. 29 is a sectional view of the interbody/intravertebral body segment of FIG. 28 taken along line 29-29 thereof.
Figure 31:
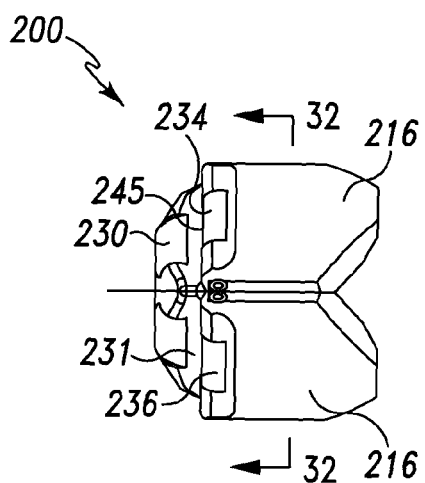
FIG. 31 is a side view of the folded interbody/intravertebral body segment.
Figure 32:
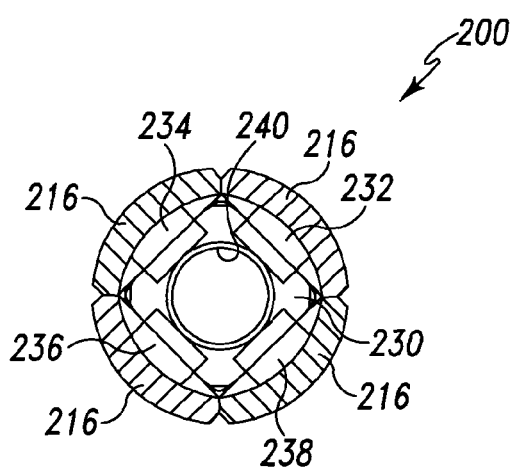
FIG. 32 is a sectional view of the folded interbody/intravertebral body segment of FIG. 31 taken along line 31-31 thereof.

As seen in FIGS. 27-32, the segments 200 include the middle or central deploy plate 214 (see FIG. 33) to which are pivotally, hingedly or swingably attached a plurality (here, four) leaf structures 212. The leaf structures 212 are pivotally attached to the deploy plate 214 by hinge pins 242 and are structured to provide a collapsed or folded position as seen in FIGS. 30-32 wherein a longitudinal axis of each leaf structure 212 is essentially co-axial with the rod 202, and an expanded or open position as seen in FIGS. 27-29 where the longitudinal axis of each leaf structure 212 is essentially perpendicular to the longitudinal axis of the rod 202. The folded position of the segments 200 provide a small diameter device, while the expanded position of the segments 200 provides a larger diameter device constrained by the length of the leaf structures 212. As illustrated in FIG. 26, the leaf bodies 216 of the segments 200 form a toothed, stepped or jagged profile.

Figure 35:
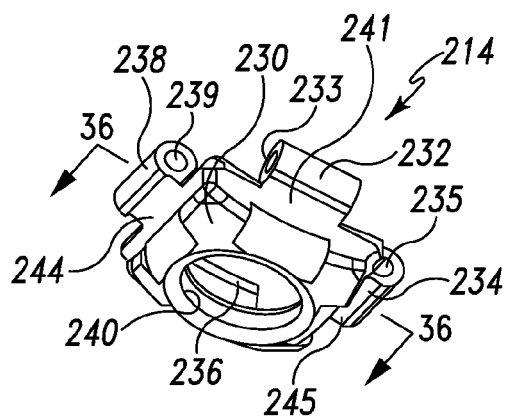
FIG. 35 is a perspective view of a deploy plate of the interbody/intravertebral body segment of the expandable interbody/intravertebral body device of FIG. 23.
Figure 36:
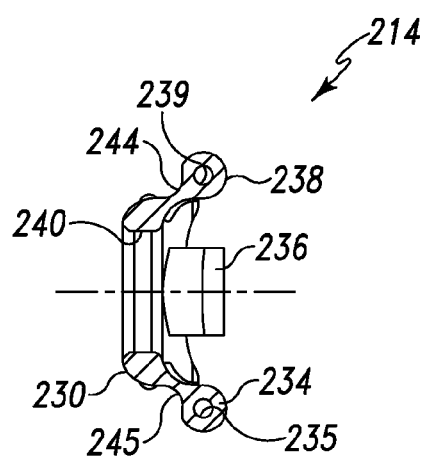
FIG. 36 is a sectional view of the deploy plate of FIG. 35 taken along line 36-36 thereof.
Figure 37:
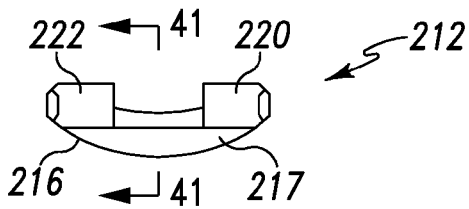
FIG. 37 is a front view of a leaf of the interbody/intravertebral body segment.
Figure 38:
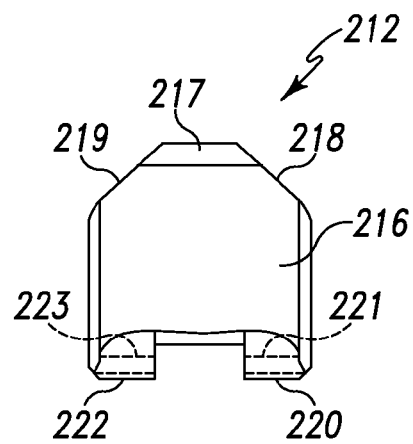
FIG. 38 is a bottom view of the leaf of the interbody/intravertebral body segment.
Figure 39:
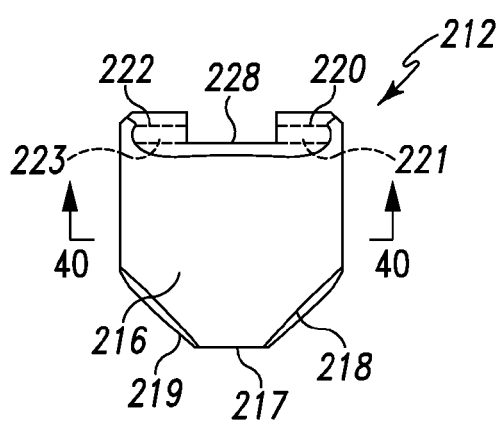
FIG. 39 is a top view of the leaf of the interbody/intravertebral body segment.
Figure 40:
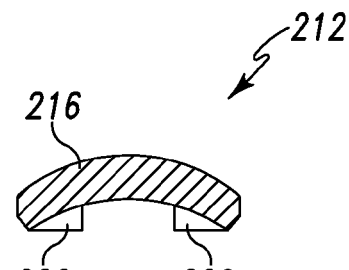
FIG. 40 is a sectional view of the leaf of the interbody/intravertebral body segment taken along line 40-40 of FIG. 39.
Figure 41:
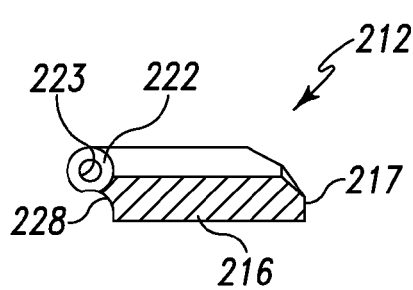
FIG. 41 is a sectional view of the leaf of the interbody/intravertebral body segment taken along line 41-41 of FIG. 37.

Referring to FIGS. 35 and 36, the deploy plate 214 of a segment 200 is particularly shown. The deploy plate 214 is characterized by a generally rectangular body 230 having a central or middle bore 240. The bore 240 is sized to be received onto the rod 202. Four cylindrical or tubular hinge structures 232, 234, 236 and 238 extend from the four sides of the body 230. Each tubular hinge structure 232, 234, 236 and 238 has a bore 233, 235, 237 and 239 respectively for receipt of a pivot pin 242. The body 230 also defines four grooves 241, 245, 231, and 244 adjacent the four hinge structures 232, 234, 236 and 238 respectively.

Referring to FIGS. 37-41 the leaf structure 212 of a segment 200 is particularly shown. A leaf structure 212 consists of a leaf body 216 having a generally "home-plate" shape (see e.g., FIGS. 38, 39) with an arched profile (see e.g., FIGS. 37, 40). As such, the body 216 includes a front 217 and two angled portions 218, 219. First and second tubular or cylindrical pivot flanges 220, 222 are provided on one side 228 of the body 216. The first flange 220 includes a bore 221 for receipt of a pivot pin 242. The second flange 222 includes a bore 223 for receipt of a pivot pin 242. The two flanges 220 and 222 are spaced from one another so as to receive a tubular flange (e.g. hinge structure 232) of the deploy plate body 230 such that the two flanges 220, 222 of the leaf body 216 straddle or are on opposite axial sides of the respective deploy plate tubular flange. In this manner a pivot pin 242 may extend through the flange 220 of the leaf body 216, the tubular flange of the deploy plate body 230, and though the flange 222 of the leaf body 216. When four leaf structures 212 are connected to the middle body 230, the leaf bodies 216 can pivot between a closed, folded or collapsed position (FIG. 30) and an open, extended or expanded position (FIG. 27).

As best seen in FIG. 28, when the leaf structures 212 are expanded, the rounded flanges 220 and 222 and flats 264 and 265 on ends of the flanges 220 and 222 of the leaf body 216 coact to provide a positive or snap feature to lock the leaf structures 212 in the expanded position.

The interbody/intravertebral body/intervertebral body device 28e, like the other interbody/intravertebral body device described herein, are designed to be delivered, installed, implanted or positioned in a patient via a cannula or tube. Such a cannula 274 is illustrated in FIGS. 44 and 45. The cannula 274 is defined by a tubular body 276 having an inner or inside surface 278. Four prongs or protrusions 280, 281, 282 and 283 are provided on the inside surface 278. These serve to guide, orient and allow expansion of the interbody/intravertebral body device 28 during implantation.

Figure 47:
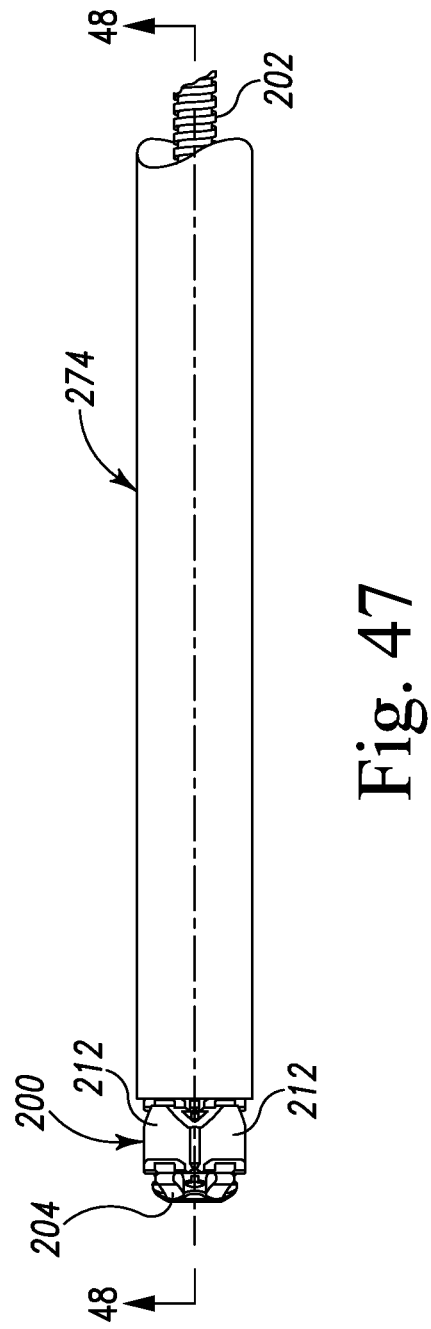
FIG. 47 is a side view of the insertion and deployment cannula of FIG. 45 holding the folded interbody/intravertebral body device of FIG. 46.

FIGS. 46-49 provide an illustration of the interbody/intravertebral body device 28e assembled for being implanted in a vertebral space. FIG. 46 shows an interbody/intravertebral body device 28e assembled and in a collapsed position. The number of segments 200 determines the overall axial length of the resulting expanded device. The assembled and collapsed interbody/intravertebral body device is provided in the cannula 274 in FIG. 47. A sectional view of FIG. 47 is provided in FIG. 48. FIG. 49 particularly depicts the juncture of the end of the cannula 274 and a segment 200 of the interbody/intravertebral body device 28e. At this point, a first segment may be deployed (expanded).

Figure 51:
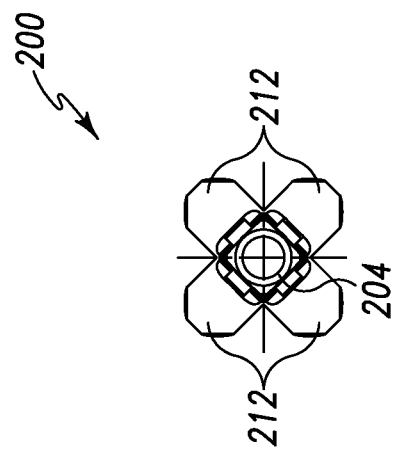
FIG. 51 is an end view of the interbody/intravertebral body device of FIG. 50 taken along line 51-51 thereof.
Figure 50:
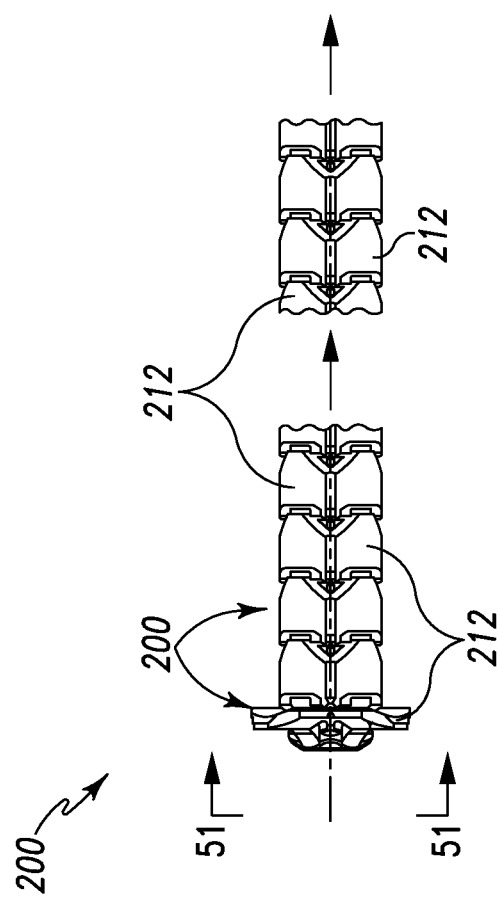
FIG. 50 is a side view of the folded expandable interbody/intravertebral body device of FIG. 46 illustrating deployment thereof.

FIGS. 50 and 51 particularly illustrate how axial compression (represented by the arrows) causes the segments 200 to expand. Particularly, axially compression causes a first segment 200 to expand. Thereafter, each successive segment expands in a somewhat "domino" effect as more axial compression is applied. In this embodiment, axial compression is provided by the nut 210. Thus, when the interbody/intravertebral body device 28e is properly placed, the nut 210 is rotated to provide axial compression until all of the segments 200 are expanded.

Figure 52:
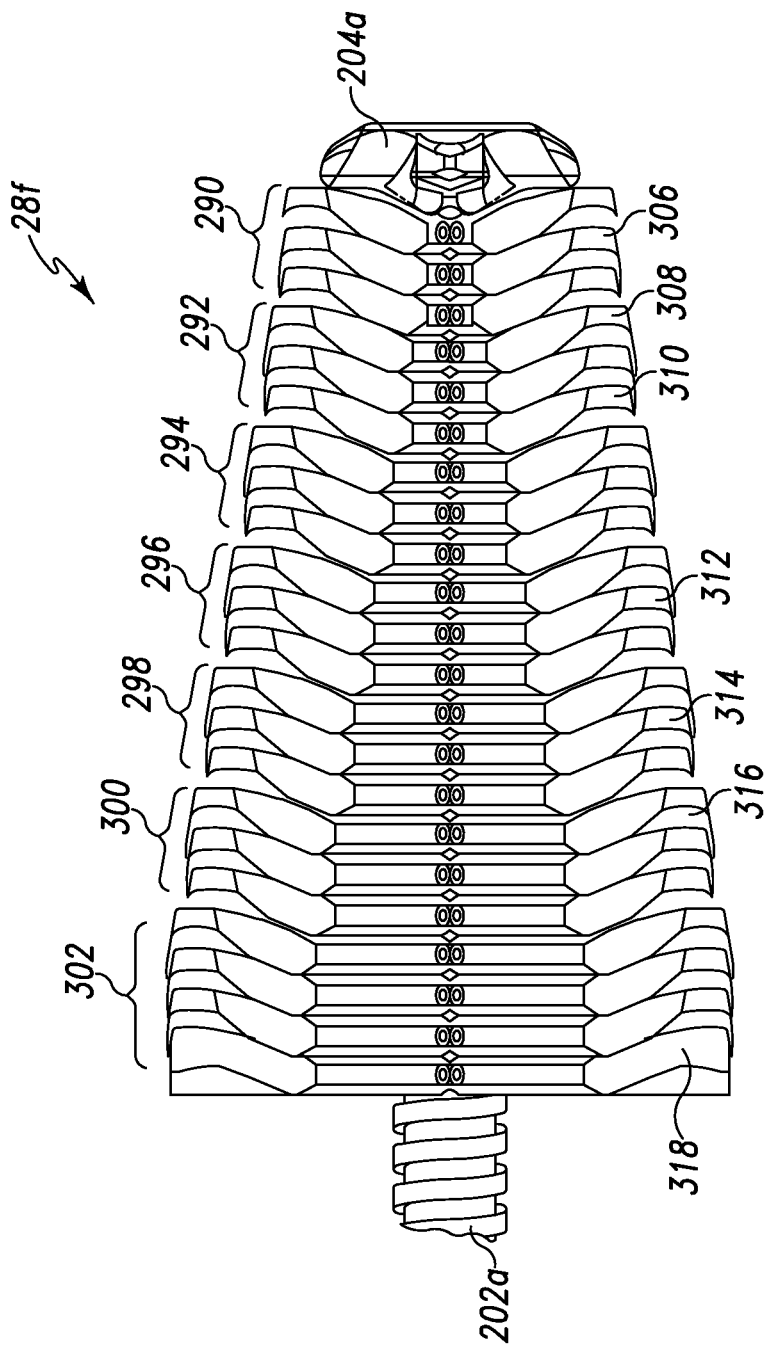
FIG. 52 is a perspective view of an exemplary embodiment of an expandable interbody/intravertebral body device in accordance with the present principles, the interbody/intravertebral body device shown in a post-implant or expanded position.
Figure 53:
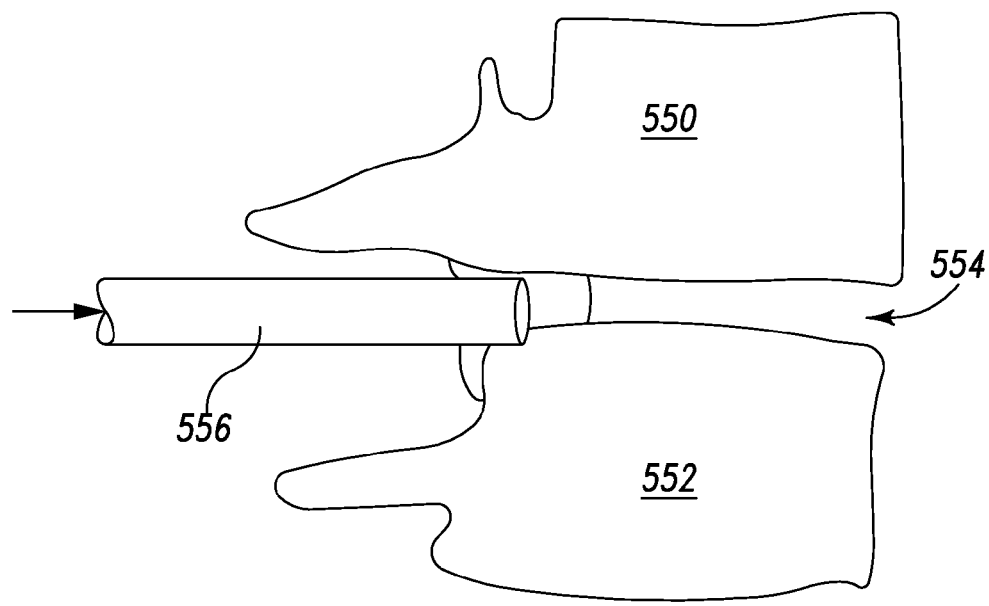
FIG. 53 is a side view of adjacent vertebrae with a cannula (insertion and deployment tube) used to introduce or implant an expandable interbody/intravertebral body device as provided herein.
Figure 54:
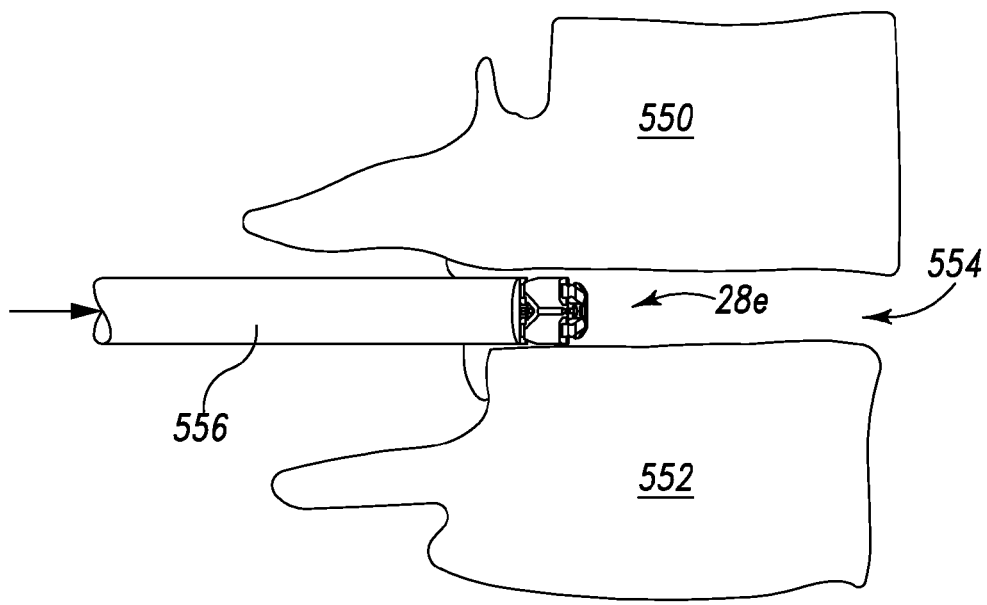
FIG. 54 is the view of FIG. 63 wherein an expandable interbody/intravertebral body device is being inserted between vertebrae.

FIG. 52 depicts an alternative embodiment or variation of the interbody/intravertebral body device 28e illustrating how different radial profiles may be created by using segments of various sizes (dimensions). In FIG. 52 there is depicted a frusto-conically shaped interbody/intravertebral body device generally designated 28f. The interbody/intravertebral body device 28f is shown in a post-implant or expanded state. The interbody/intravertebral body device 28f includes a plurality 290, 292, 294, 296, 298, 300 and 302 of groups of interbody/intravertebral body segments each group of segments 290, 292, 294, 296, 298, 300 and 302 having respective leaves 306, 308, 310, 312, 314, 316 and 318 of different radial height. As can be appreciated, the axial length of any group 290, 292, 294, 296, 298, 300 and 302 is determined by the number of segments in the group. The radial height or profile of each group 290, 292, 294, 296, 298, 300 and 302 is determined by the radial height of the leaf structures (and the middle plate) of the segments. A multitude of radial profiles may be created.

It should be appreciated that the segments 200 of the various interbody/intravertebral body devices may or may not be at least limitedly movable relative to one another. In one case, the segments 200 are fixed relative to each other and therefore no movement can occur between the segments. In another case, the segments 200 are at least limitedly movable radially with respect to another segment 200 such that the interbody/intravertebral body is dynamic. This allows for limited movement within the interbody/intravertebral body device itself.

Figure 55:
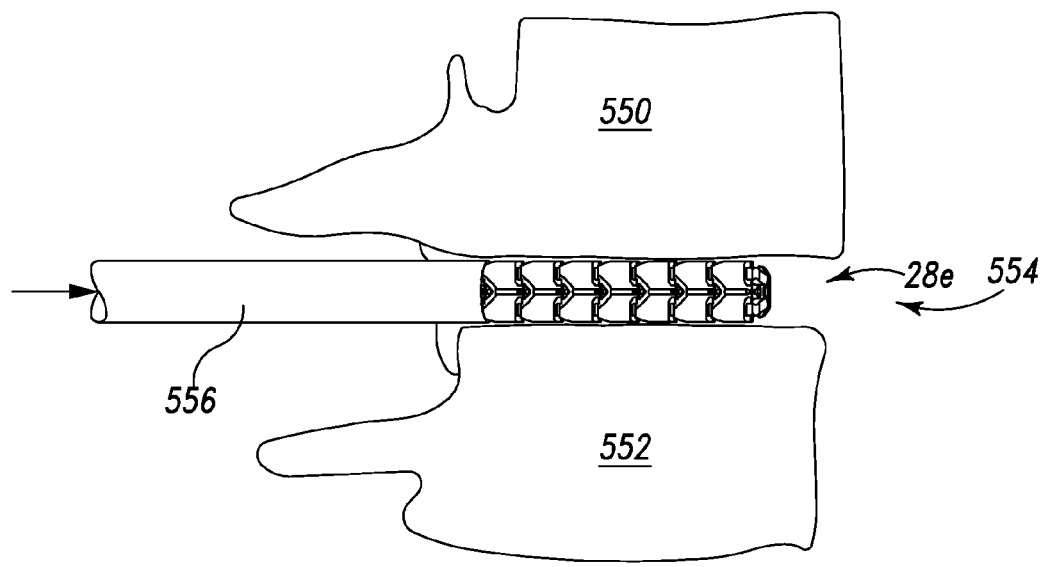
FIG. 55 is the view of FIG. 63 wherein the expandable interbody/intravertebral body device has been properly positioned for expansion/deployment.
Figure 56:
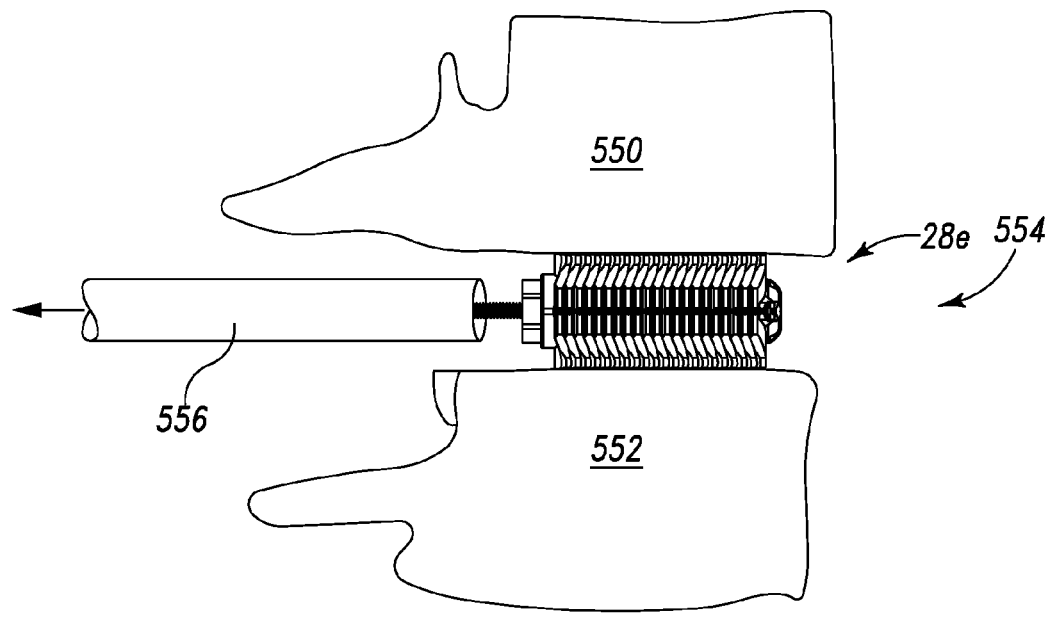
FIG. 56 is the view of FIG. 63 wherein the expandable interbody/intravertebral body device has been fully expanded or deployed.

Referring lastly to FIGS. 53-56, there is illustrated a manner of implanting the interbody/intravertebral body devices 28a-28f. Particularly, but without restriction or being necessarily so, the various interbody/intravertebral body devices 28a-28f are percutaneously implanted via a cannula 556. The end of the cannula 556 is positioned proximate an intervertebral space 554 between a first vertebra 550 and a second vertebra 552. The particular interbody/intravertebral body device (here, interbody/intravertebral body device 28e is shown) is then inserted into the cannula 556 as represented by the arrow. Once the particular interbody/intravertebral body device is appropriately placed in the intervertebral space 554, the interbody/intravertebral body device is expanded via an appropriate instrument through the cannula 556. As shown in FIG. 55 the interbody/intravertebral body device 28e is received in the vertebral space 554. In FIG. 56, the interbody/intravertebral body device 28e has been radially expanded to vertically fill the vertebral space 554 through axial compression of the segments 200 of the interbody/intravertebral body device 28e.

Figure 57:
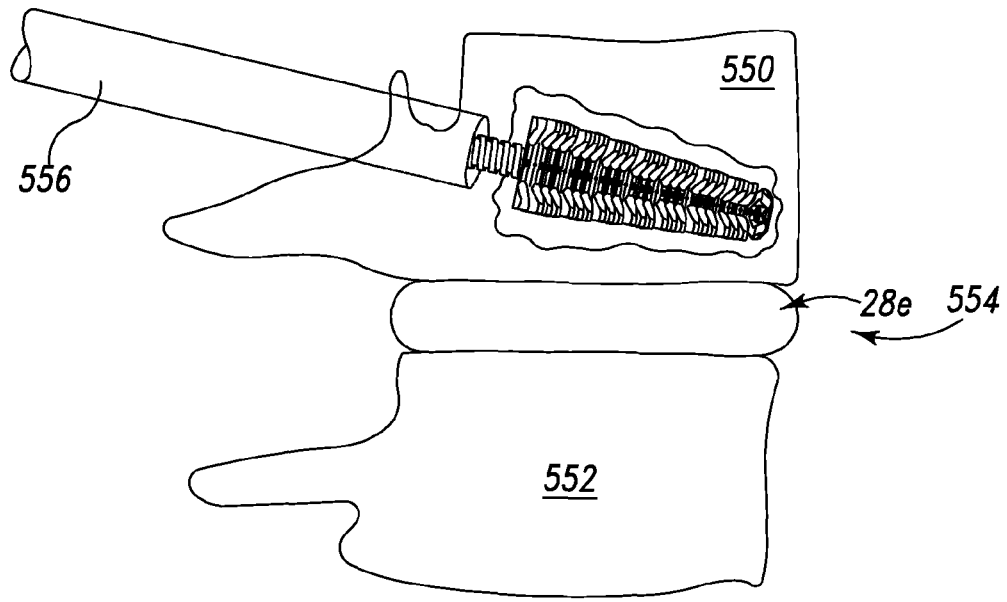
FIG. 57 is side view of a portion of a spinal column showing two adjacent vertebrae with a cannula (insertion and deployment tube) used to introduce or implant an expandable interbody/intravertebral body device as an intravertebral body device, the expandable intravertebral body device shown in an unexpanded position.
Figure 58:
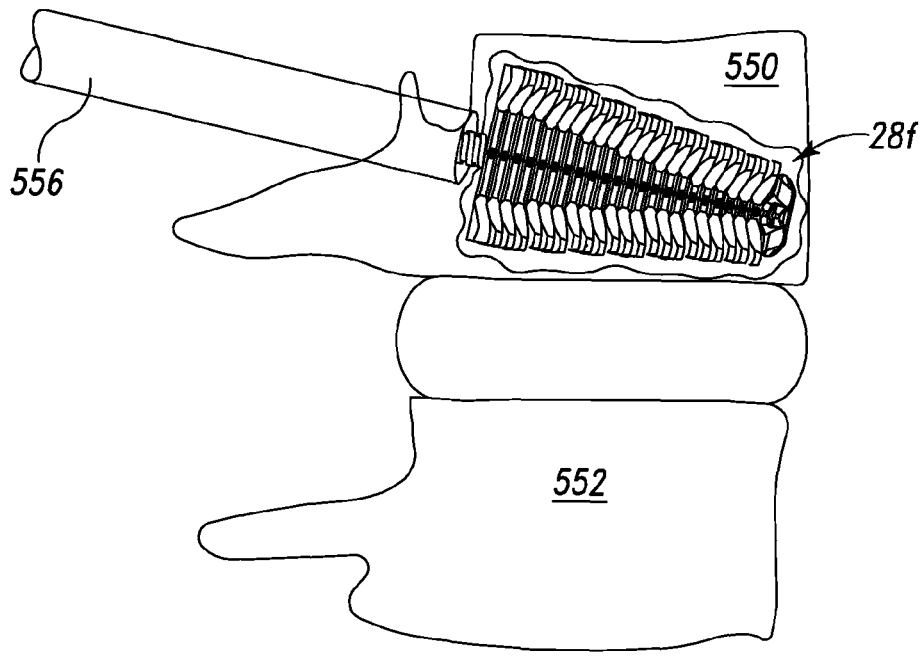
FIG. 58 is the view of FIG. 57 wherein the expandable intravertebral device is shown in an expanded position within the vertebra.

FIGS. 57 and 58 illustrate use of a spinal body 28 as an intravertebral body device. Particularly interbody/intravertebral body 28f is shown in FIG. 57 as implanted via cannula 556 into vertebra 550 (intravertebral). The intravertebral device 28f is initially unexpanded. In FIG. 58, the intravertebral device 28f has been expanded within the vertebra. This use is applicable to treat vertebral compression fractures and/or the like.

It should be appreciated that each interbody/intravertebral body device 28a through 28e may be scaled to any size necessary. Additionally, each interbody/intravertebral body device 28a-28e is manufactured from a bio-compatible material such as a titanium-based metal. Variations are also contemplated.

Referring now to FIGS. 59-74, a radially expandable implant 610 (e.g., an interbody device, and intrabody device, etc.) is shown according to an exemplary embodiment. Implant 610 is usable, for example, between and/or within vertebral bodies of the spine, and may share many of the features of the other inter/intra-body implants discussed elsewhere herein. However, it should be understood that implant 610 may have other uses in other portions of a patient's body (e.g., inside or around bone, such as a femur, as a cement restrictor, etc.). All such applications are understood to be within the scope of the present disclosure.

Figure 61:
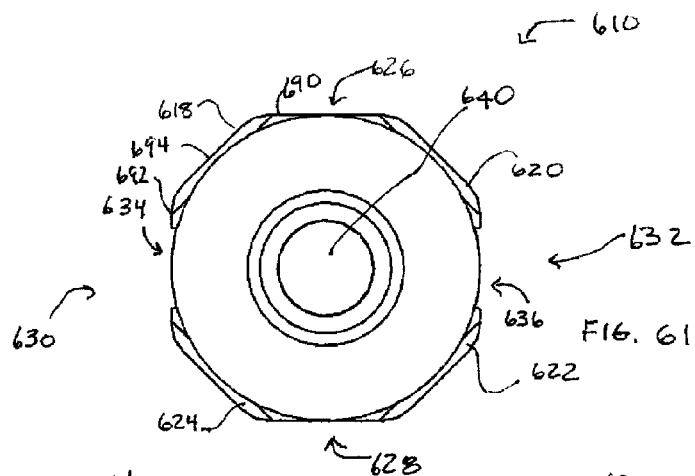
FIG. 61 is a front view of the implant of FIG. 59 according to an exemplary embodiment.

According to an exemplary embodiment, implant 610 includes a first portion 612 (e.g., a front member or portion, a narrowing member, a rounded member, etc.), a second portion 614 (e.g., a rear member or portion, a moveable member, etc.), and a third portion or control member 616 (e.g., a control rod or member, an intermediate member, a coupling member, etc.). First and second portions 12, 14 and control member 616 form a body assembly for implant 610 that extends along a longitudinal axis 688. A plurality of supports 618, 620, 622, 624 (e.g., moveable supports, elongated members, wings, etc.) are coupled to the body assembly and extend generally parallel to longitudinal axis 688. In one embodiment, as shown in FIG. 61, supports 618, 620, 622, 624 define a top and bottom 626, 628, and first and second sides 630, 632, of implant 610. Top and bottom 626, 628 define a height of implant 610, and first and second sides 630, 632 define a width of implant 610. First and second sides 630, 632 include longitudinal extending gaps, or spaces, 634, 636.

Figure 59:
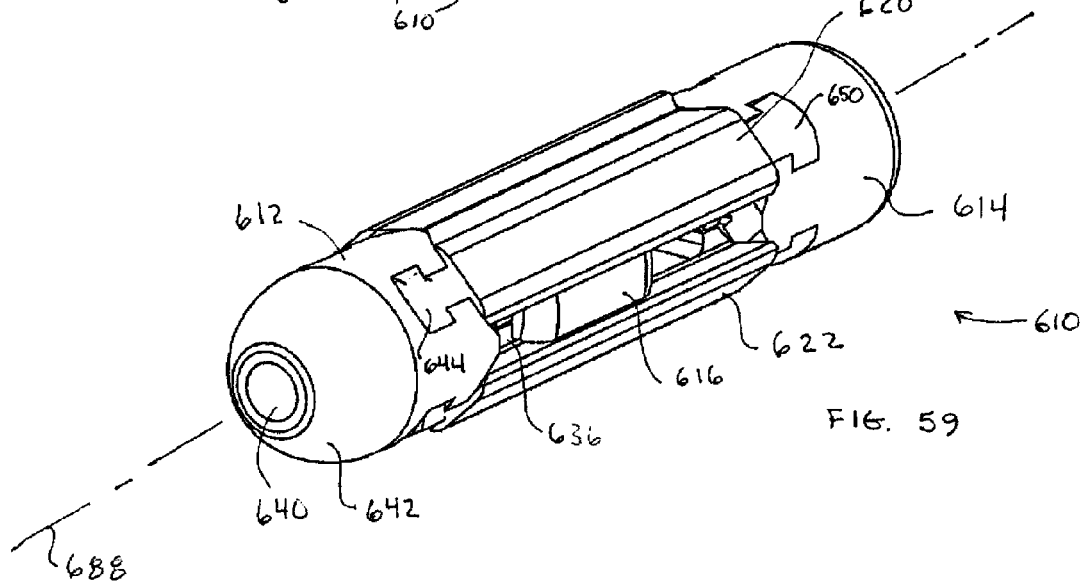
FIG. 59 is a perspective view of an implant in a collapsed configuration according to an exemplary embodiment.
Figure 68:
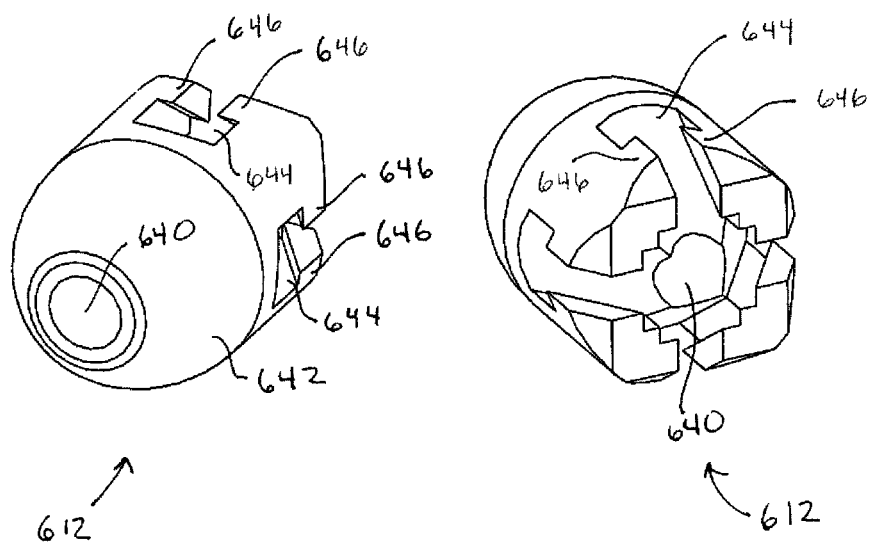
FIG. 68 is a perspective view of a front portion of the implant of FIG. 59 according to an exemplary embodiment.
Figure 69:
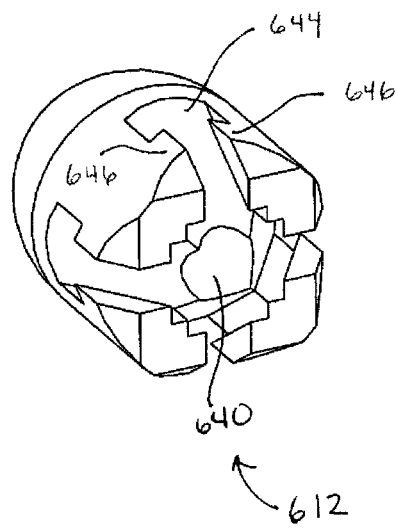
FIG. 69 is another perspective view of the front portion of FIG. 68 according to an exemplary embodiment.

As shown in FIGS. 59 and 68-69, first portion 612 includes a central bore 640 that receives control member 616. In some embodiments, first member 612 may threadingly receive control member 616. In other embodiments, first portion 612 and control member 616 may be integrally formed, welded, or coupled using any other suitable joining method. In some embodiments, first portion 612 may be rotationally and longitudinally fixed relative to control member 616. In other embodiments, first portion 612 may be longitudinally and/or rotationally moveable relative to control member 616.

First portion 612 further includes a tip portion 642 that may be rounded, bull-nosed, or otherwise have a contoured forward portion configured to facilitate insertion of implant 610 into a desired location with a patient (e.g., in a spinal space, etc.). First portion 612 may be generally cylindrical in shape rearward of tip portion 642, and may include a plurality of guide channels 644 configured to receive portions (e.g., first ends) of supports 618, 620, 622, 624. According to an exemplary embodiment, guide channels 644 are generally T-shaped and are formed in part by a pair of projections 646. In one embodiment, one guide channel 644 is provided for each support 618, 620, 622, 624, and guide channels 644 are equally spaced about the circumference of first portion 612. In other embodiments, more or fewer guide channels 644 may be provided, and the shape, location, and/or spacing of the guide channels may be varied.

Figure 70:
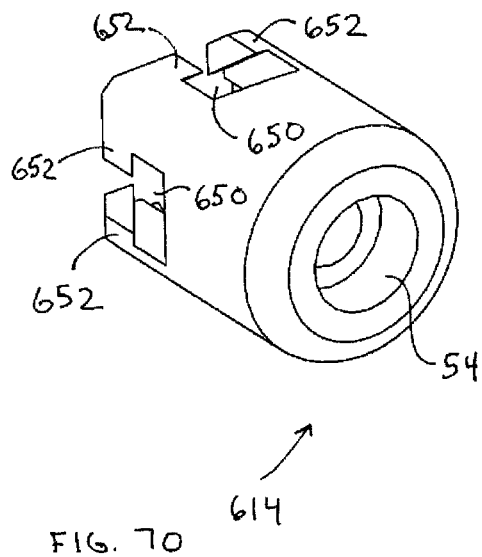
FIG. 70 is a perspective view of a rear portion of the implant of FIG. 59 according to an exemplary embodiment.
Figure 71:
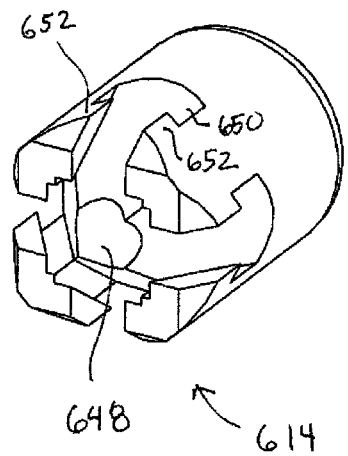
FIG. 71 is another perspective view of the rear portion of FIG. 70 according to an exemplary embodiment.

As shown in FIGS. 67 and 70-71, second portion 614 includes a central bore 648 that receives control member 616. In some embodiments, second portion 614 may be longitudinally moveable relative to control member 616 so as to vary the distance between first portion 612 and second portion 614. Second portion 614 may be generally cylindrical in shape rearward of tip portion 642, and may include a plurality of guide channels 650 configured to receive portions (e.g., second ends) of supports 618, 620, 622, 624. According to an exemplary embodiment, guide channels 650 are generally T-shaped and are formed in part by a pair of projections 652. In one embodiment, one guide channel 650 is provided for each support 618, 620, 622, 624, and guide channels 650 are equally spaced about the circumference of second portion 614. In other embodiments, more or fewer guide channels 650 may be provided, and the shape, location, and/or spacing of the guide channels may be varied.

According to an exemplary embodiment, the rearward end of second portion 614 includes a counterbore 654 configured to receive a collar 638 (e.g., a threaded collar, etc.). Collar 638 is configured to be received at least partially within counterbore 654 and be threadingly received on a threaded end 696 of control member 616. As the position of collar 638 changes longitudinally along control member 616, the position of second portion 614 relative to first portion 612 changes. As discussed in further detail below, rotation of collar 638 about control member 616 may be usable to control the distance between first and second portions 612, 614, and in turn the amount of radial expansion of supports 618, 620, 622, 624.

Figure 60:
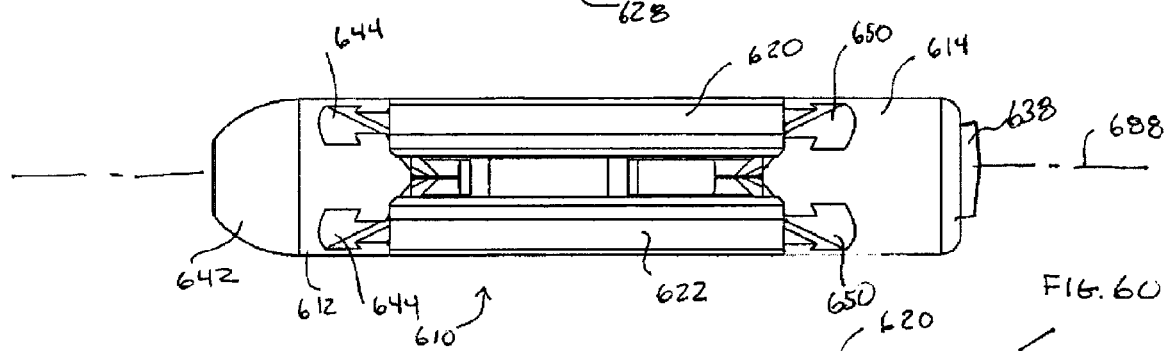
FIG. 60 is a side view of the implant of FIG. 59 according to an exemplary embodiment.
Figure 64:
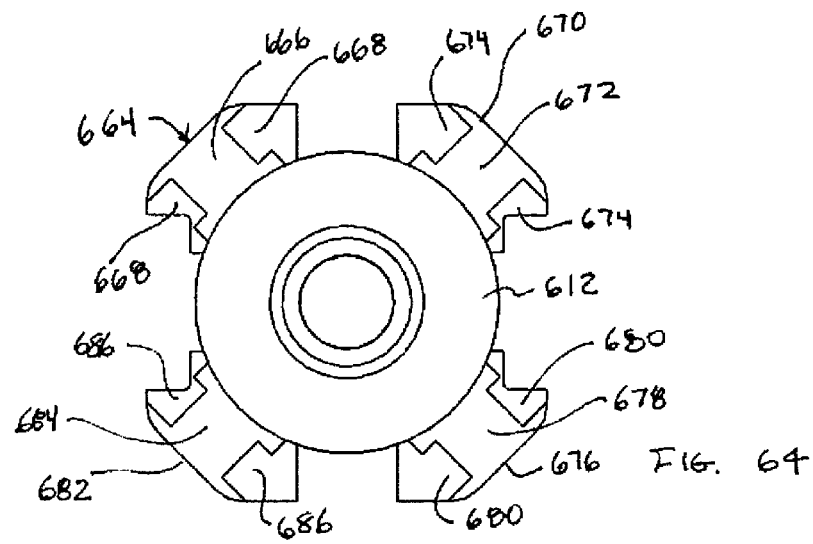
FIG. 64 is a front view of the implant of FIG. 59 in an expanded configuration according to an exemplary embodiment.
Figure 63:
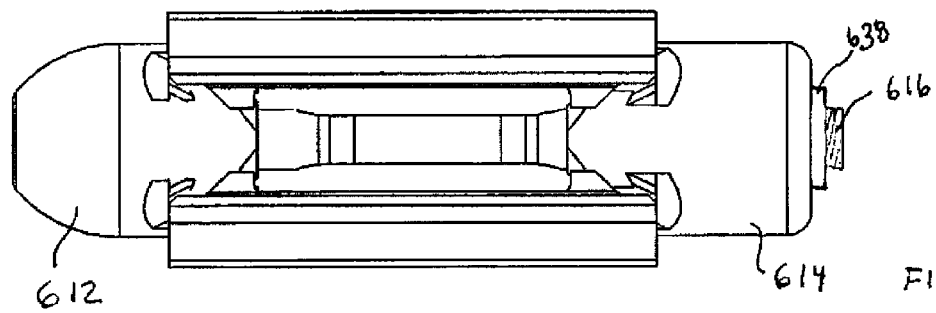
FIG. 63 is a side view of the implant of FIG. 59 is an expanded configuration according to an exemplary embodiment.
Figure 62:
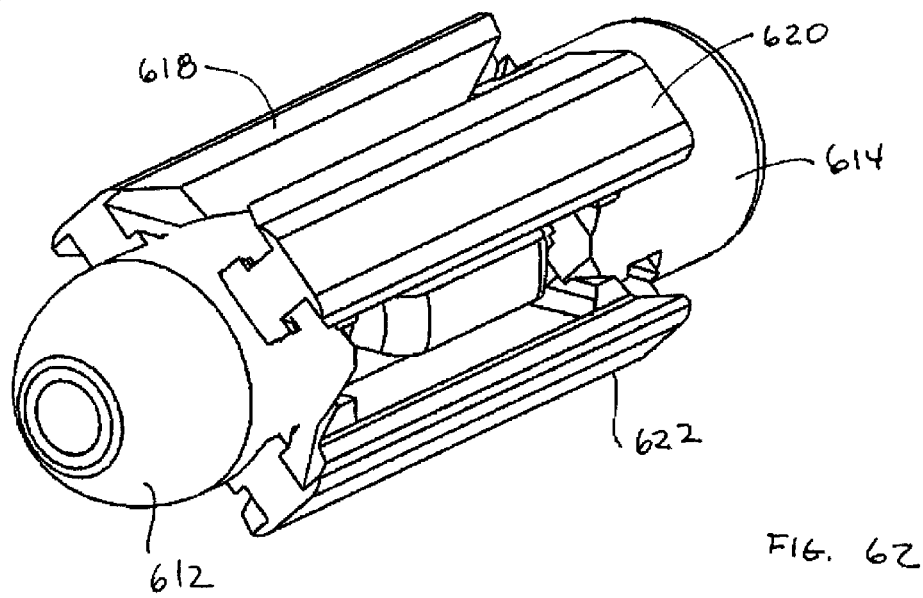
FIG. 62 is a perspective view of the implant of FIG. 59 in an expanded configuration according to an exemplary embodiment.

In one embodiment, supports 618, 620, 622, 624 are configured to be moveable relative to the body assembly (e.g., first and second portions 612, 614 and control member 616) in a radially outward direction (e.g., generally perpendicular to longitudinal axis 688) such that implant 610 is reconfigurable between a first configuration (e.g., a retracted, collapsed, or minimal configuration) as shown in FIGS. 59-61, and a second configuration (e.g., an expanded or maximum configuration), as shown in FIGS. 62-64.

Referring to FIGS. 65-67, according to an exemplary embodiment, first portion 612 is fixedly coupled to control member 616, and second portion 614 is moveably coupled to control member 616. For example, in one embodiment, second portion 614 is slidable along at least a portion of control member 616 (e.g., by rotation of collar 638) such that the longitudinal distance between first and second portions 612, 614 is adjustable. Supports 618, 620, 622, 624 are coupled to first and second portions 612, 614 such that supports 618, 620, 622, 624 are moveable between expanded and collapsed positions by moving second portion 614 toward or away from first portion 612 along control member 616.

According to an exemplary embodiment shown in FIGS. 61-62, 65, and 67, supports 618, 620, 622, 624 and first and second portions 612, 614 have corresponding geometry that causes the longitudinal displacement of second portion 614 relative to first portion 612 to result in inward or outward radial movement of support 618, 620, 622, 624. For example, in one embodiment, as second portion 614 moves toward first portion 612 (e.g., as the distance between first and second portions 612, 614 decreases), supports 618, 620, 622, 624 move radially outward, and as second portion 614 moves away from first portion 612 (e.g., as the distance between first and second portions 612, 614 increases), supports 618, 620, 622, 624 move radially inward. In one embodiment, support 618 is located opposite from and moves in an opposite radial manner relative to support 622, and support 620 is located opposite from and moves in an opposite radial manner relative to support 624. Furthermore, support 618, 622 are generally perpendicularly arranged relative to supports 620, 624, and supports 618, 622 move in perpendicular directions relative to supports 620, 624.

According to one embodiment, supports 618, 620, 622, 624 have similar structures to each other and are moveably coupled to first and second portions 612, 614 in similar fashions. For example, referring to FIGS. 72-74, support 618 is a generally elongated member that extends at least partially between first and second portions 612, 614. In one embodiment, support 618 includes an outer surface 664, and may be configured such that all or a portion of outer surface 664 extends longitudinally beyond first portion 612 and/or second portion 614 when implant 610 is in the first or collapsed configuration.

Figure 74:
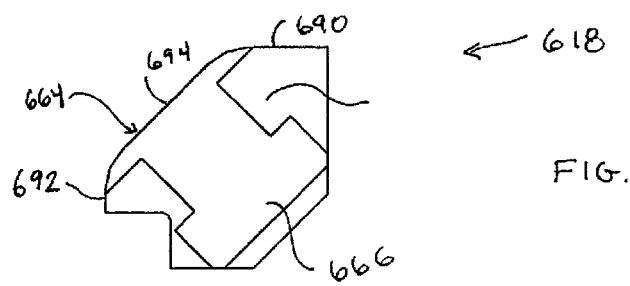
FIG. 74 is a front view of the support member of FIG. 72 according to an exemplary embodiment.
Figure 72:
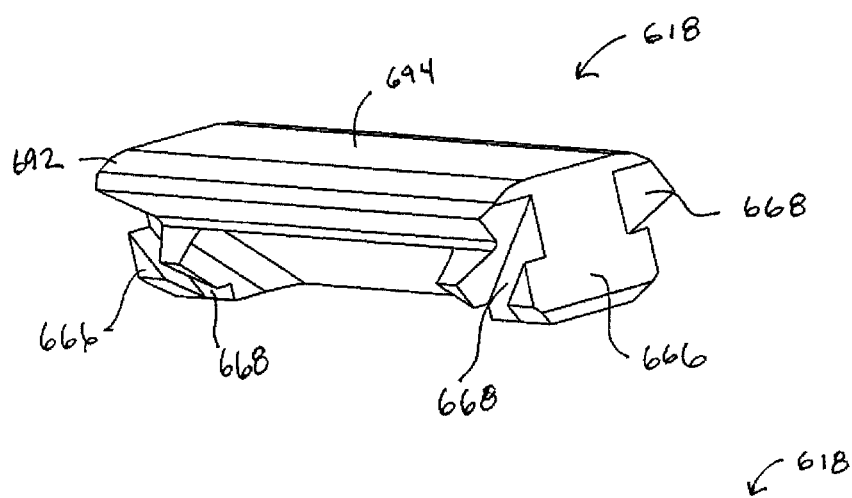
FIG. 72 is a perspective view of a support member of the implant of FIG. 59 according to an exemplary embodiment.
Figure 73:
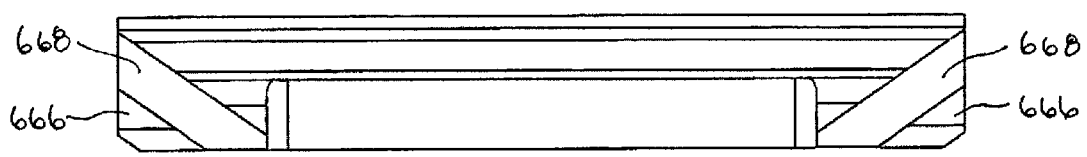
FIG. 73 is a side view of the support member of FIG. 72 according to an exemplary embodiment.

According to an exemplary embodiment shown in FIGS. 72-74, support 618 includes an outer surface 664, a portion 690 of which defines top 626 of implant 610 and a portion 692 of which defines first side 630 of implant 610. Portions 690, 692 are generally perpendicular relative to one another and are joined by a middle surface 694 (e.g., FIG. 74). In some embodiments, surface portions 690, 692 each extend from middle portion 694 at an obtuse angle (e.g., an angle of approximately 135 degrees), while in other embodiments the angular relationships between surface portions 690, 692, 694 may be of other angular values. As shown in the FIGURES, surface portions 690, 692, 694 are generally planar surfaces that extend in a parallel fashion relative to longitudinal axis 688. In other embodiments, surface portions 690, 692, 694 may be non-planar (e.g., curved, concave, convex, irregularly contoured, etc.) and/or be non-parallel relative to longitudinal axis 688. Furthermore, surface portions 690, 692, 694 may be smooth, textured, provided with ridges, teeth, projections (e.g., for gripping adjacent bone material), and the like.

Support 618 includes a guide portion 666 (e.g., a projection, etc.) provided at each end of support 618. Guide portion 666 may be generally T-shaped and may be formed by a pair of channels 668 that extend at an angle (e.g., 45 degrees, etc.) relative to longitudinal axis 688. While guide portion 666 is shown as having a general T-shape, according to various alternative embodiments, guide portion 666 may take any suitable shape. Guide portions 666 are slidably received within guide channels 644, 650 of first and second portions 612, 614, respectively, so as to adjustably couple support 618 to first and second portions 612, 614. According to one embodiment, guide portions 666 and guide channels 644, 650 include mating sliding surfaces that extend at an angle of approximately 45 degrees relative to longitudinal axis 688. According to various alternative embodiments, the mating sliding surfaces of guide portions 666 and guide channels 644, 650 may extend at other angles relative to longitudinal axis 688 (e.g., at angles of more or less than 45 degrees).

Supports 620, 622, 624 include similar features to support 618. For example, support 620 includes an outer surface 670, guide portions 672, and guide channels 674. Support 622 includes an outer surface 676, guide portions 678, and guide channels 680. Support 624 includes an outer surface 682, guide portions 684, and guide channels 686. Supports 620, 622, 624 are coupled to and move relative to first and second portions 612, 614 in the same manner as support 618. According to one embodiment, supports 618 and 622 are substantially identical in structure and are mirror images of supports 620, 624. In other embodiments, each support may have a different structure.

According to an exemplary embodiment, control member 616 is an elongated member that extends between first and second portions 612, 614. Control member 616 includes a cavity, or graft chamber 662 located generally at the midpoint of control member 616. Chamber 662 is configured to receive bone growth or other materials to facilitate growth of bone, etc. in and around implant 610. Chamber 662 is in one embodiment generally rectangular in shape, while in other embodiments, chamber 662 may take other shapes, including square, circular, oval, irregular shapes, etc. In some embodiments, control member 616 may be generally cylindrical in shape to either side of chamber 662, and one or both ends of control member 616 may be threaded to facilitate coupling of control member 616 to collar 638 and/or first portion 612.

Referring to FIGS. 59-61, in one embodiment, outer surfaces 664, 670 of supports 618, 620 and surfaces 676, 682 of supports 620, 622 are generally adjacent one another to form continuous top and bottom surfaces for implant 610 when implant 610 is in the first or collapsed configuration. To accommodate chamber 662, supports 618, 620, 622, 624 define side gaps, or spaces 634, 636 that are sized to accommodate chamber 662 and facilitate the introduction of bone growth or other material into the interior of chamber 662.

In use, implant 610 may initially be in the first or retracted configuration, as shown in FIGS. 59-61. Implant 610 may be inserted into a patient in a desired position (e.g., into or adjacent a vertebral body, etc.) using a suitable installation tool. Once in a desired position, implant 610 may be radially expanded to an expanded configuration, as shown in FIGS. 62-64. To expand/collapse implant 610, a tool (e.g., a screw driver, wrench, etc.) may be used to rotate collar 638 about control member 616 to move collar 638 and second portion 614 along control member 616 and adjust the longitudinal spacing between first and second portions 612, 614 (e.g., closer or further apart) and the radial expansion of supports 618, 620, 622, 624 (expansion and retraction).

In some embodiments, the angular relationships between the outer surfaces 664, 670, 676, 682 of supports 618, 620, 622, 624 remains constant as the supports are expanded/collapsed. In other embodiments, supports 618, 620, 622, 624 move linearly and radially outward, such that supports 618, 620, 622, 624 do not rotate relative to axis 688 when moving between the collapsed and expanded configurations.

In the expanded configuration, supports 618, 620, 622, 624 may be positioned so as to form a generally X-shaped support. This configuration may reduce the chance of the implant tipping over relative to other-shaped implants (e.g., circular or oval). Furthermore, as shown in FIG. 64, both the height and width of implant 610 are increased during expansion of implant 610, providing a benefit over many conventional expandable implants that may expand only in height. In other embodiments, supports 618, 620, 622, 624 may form other shapes in the expanded configuration. Furthermore, while the FIGURES generally illustrate implant 610 in either a fully collapsed or fully expanded configuration, it should be understood that implant 610, through rotation of collar 638 or another suitable adjustment mechanism, may be expanded to any intermediate level of expansion. Further yet, in some embodiments, implant 610 may be expandable to approximately double a height and width of implant 610.

According to various exemplary embodiments, the components of implant 610 may be made of any suitable material(s), including a variety of metals, plastics, composites, or other suitable bio-compatible materials. In some embodiments, one or more components of implant 610 may be made of the same material, while in other embodiments, different materials may be used for different components of implant 610.

It is important to note that the construction and arrangement of the elements of the various implants and implant components as shown in the exemplary embodiments are illustrative only. Although a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, materials, colors, orientations, etc.) without materially departing from the novel teachings and advantages of the subject matter recited in the various embodiments. Accordingly, all such modifications are intended to be included within the scope of the present disclosure as defined in the appended claims. The order or sequence of any process or method steps may be varied or re-sequenced according to alternative embodiments. Other substitutions, modifications, changes, and/or omissions may be made in the design, operating conditions, and arrangement of the exemplary embodiments without departing from the spirit of the present disclosure.

What is claimed is:

1. An implant for insertion into a spinal space, the implant comprising:
   a body assembly, the body assembly comprising a first portion moveably coupled to a second portion by a control member along a longitudinal axis; and
   a plurality of support members disposed at least partially between the first portion and the second portion, the plurality of support members including four support members;
   wherein movement of the second portion relative to the first portion along the longitudinal axis causes the plurality of support members to move radially relative to the longitudinal axis;
   wherein the plurality of support members slidably engage the first and second portions of the body as the support members move radially relative to the longitudinal axis; and
   wherein the control member includes a first generally cylindrical end received within the first portion, a second generally cylindrical end received within the second portion, and a rectangular shaped portion defining a bone graft cavity disposed between the first end and the second end.

2. The implant of claim 1, wherein the first portion is fixedly coupled to the control member and the second portion is slidably received on the control member.

3. The implant of claim 2, further comprising a collar threadingly received on the control member adjacent the second portion, wherein rotation of the collar about the control member moves the second portion relative to the first portion and causes the plurality of support members to move radially relative to the longitudinal axis.

4. The implant of claim 1, wherein each of the plurality of support members comprises a first end having a first projection received in a corresponding first channel in the first portion, and a second end having a second projection received in a corresponding second channel in the second portion.

5. The implant of claim 4, wherein each first projection comprises a surface that slidingly engages the first channel in a plane extending at about 45 degrees relative to the longitudinal axis, and wherein each second projection comprises a surface that slidingly engages the second channel in a plane extending at about 45 degrees relative to the longitudinal axis.

6. The implant of claim 1, wherein the four support members are configured to increase the peripheral height and width of the implant upon the plurality of support members being radially expanded.

7. The implant of claim 6, wherein the four support members are generally equally circumferentially spaced about the first and second portions.

8. The implant of claim 1, wherein each of the plurality of support members is an elongated member extending generally parallel to the longitudinal axis, and each of the plurality of support members moves linearly radially outward in a direction generally perpendicular to the longitudinal axis when expanded.

9. The implant of claim 1, wherein adjacent ones of the plurality of support portions move relative to one another at an angle less than 180 degrees.

10. An implant comprising:
    a front portion;
    a rear portion;
    an intermediate portion coupled to the front portion and the rear portion and defining a longitudinal axis, wherein the intermediate portion includes a first generally cylindrical end received within the front portion, a second generally cylindrical end received within the rear portion, and a rectangular shaped portion defining a bone graft cavity disposed between the first and the second end; and
    a plurality of support members configured to move radially outward relative to the longitudinal axis in a linear fashion as the rear portion moves toward the front forward portion to increase a height and a width of the implant.

11. The implant of claim 10, wherein the plurality of support members slidably engage the front and rear portions as the plurality of support members move between a radially collapsed configuration and a radially expanded configuration.

12. The implant of claim 10, wherein the plurality of support members each include outward-facing surfaces configured to engage vertebral bodies.

13. The implant of claim 12, wherein the angular relationships between the outward-facing surfaces remains constant as the plurality of support members move radially.

14. The implant of claim 10, wherein the plurality of support members are expandable to approximately double a height and a width of the implant.

15. The implant of claim 10, wherein the front portion is fixedly coupled to the intermediate portion and the rear portion is moveably coupled to the intermediate portion.

16. The implant of claim 10, wherein the plurality of support members comprises at least three support members.

17. An implant for insertion into a spinal space, the implant comprising:
    a body portion; and
    a plurality of support portions coupled to the body portion and moveable relative to the body portion in a linear radial direction to increase a height and a width of the implant;
    wherein adjacent ones of the plurality of support portions move relative to one another at non-straight angles;
    wherein the plurality of support portions include four support portions that define first and second coplanar upper surfaces configured to engage vertebral bodies and first and second coplanar lower surfaces configured to engage vertebral bodies; and
    wherein the plurality of support portions slidably engage the body portion as the plurality of support portions move relative to the body portion in the linear radial direction.

18. The implant of claim 17, wherein the plurality of support portions form an X-shaped support when the plurality of support portions are moved into an expanded configuration.

19. The implant of claim 17, wherein the body portion comprises a rearward portion adjustably coupled to a forward portion such that adjustment of the rearward portion relative to the forward portion causes linear radial movement of the plurality of support portions.

20. The implant of claim 19, wherein the body portion comprises a control member and a collar threadingly received on the control member such that threadingly moving the collar along the control member causes adjustment of the rearward portion relative to the forward portion.

* * * * *

UNITED STATES PATENT AND TRADEMARK OFFICE
CERTIFICATE OF CORRECTION

| | | |
|---|---|---|
| PATENT NO. | : 8,940,048 B2 | Page 1 of 1 |
| APPLICATION NO. | : 13/615273 | |
| DATED | : January 27, 2015 | |
| INVENTOR(S) | : Michael S. Butler and Daniel Predick | |

It is certified that error appears in the above-identified patent and that said Letters Patent is hereby corrected as shown below:

In the Claims

Claim 10:

Column 18, line 16, delete "forward" after "front"

Signed and Sealed this
Twenty-first Day of July, 2015

Michelle K. Lee
*Director of the United States Patent and Trademark Office*